US010631762B2

(12) United States Patent
Kelarakis et al.

(10) Patent No.: US 10,631,762 B2
(45) Date of Patent: Apr. 28, 2020

(54) METHOD OF FINGERPRINTING WITH USING CARBOGENIC NANOPARTICLE

(71) Applicant: University of Central Lancashire, Preston, Lancashire (GB)

(72) Inventors: Antonios Kelarakis, Preston (GB); Marta J Krysmann, Preston (GB); Diogo Fernandes, Preston (GB)

(73) Assignee: University of Central Lancashire, Preston, Lancashire (GB)

( * ) Notice: Subject to any disclaimer, the term of this patent is extended or adjusted under 35 U.S.C. 154(b) by 0 days.

(21) Appl. No.: 15/512,119

(22) PCT Filed: Sep. 18, 2015

(86) PCT No.: PCT/GB2015/052698
§ 371 (c)(1),
(2) Date: Mar. 17, 2017

(87) PCT Pub. No.: WO2016/042337
PCT Pub. Date: Mar. 24, 2016

(65) Prior Publication Data
US 2017/0281053 A1    Oct. 5, 2017

(30) Foreign Application Priority Data
Sep. 19, 2014    (GB) .................................. 1416602.9

(51) Int. Cl.
*A61B 5/117*    (2016.01)
*A61B 5/1172*    (2016.01)
(Continued)

(52) U.S. Cl.
CPC ............ *A61B 5/117* (2013.01); *A61B 5/1172* (2013.01); *G06K 9/00006* (2013.01); *A61B 5/1171* (2016.02); *G06K 9/00* (2013.01)

(58) Field of Classification Search
CPC ..... A61B 5/1172; A61B 5/117; A61B 5/1171; G06K 9/00006; G06K 9/00
(Continued)

(56) References Cited

U.S. PATENT DOCUMENTS 4,226,740 A    10/1980 Worsham et al.
4,708,882 A  * 11/1987 Asano .................. A61B 5/1172
                                                        427/1
(Continued)

FOREIGN PATENT DOCUMENTS

EP         1919361 B1     3/2014
WO       2010007443 A2    1/2010
WO      WO2012016296   *  2/2012

OTHER PUBLICATIONS

Krysmann, et al. (Formation Mechanism of Carbogenic Nanoparticles with Dual Photoluminescence Emission), Cornell University, NY, pp. 747-750, . (Year: 2011).*

*Primary Examiner* — Daniel G Mariam
(74) *Attorney, Agent, or Firm* — Burns & Levinson LLP; Shawn P. Foley

(57) ABSTRACT

The present invention relates to a powder composition, in particular a fingerprint powder composition for the visualisation of latent fingerprints. Such fingerprint powder compositions comprise carbogenic nanoparticles which, when mixed with a suitable diluent (including any existing or future fingerprint powders), exhibits excitation-dependent emission properties which enable the fingerprint powder compositions and imagable fingerprint impression patterns formed therefrom to be imaged in a variety of different colours by simply varying the wavelength(s) of any excitation radiation. As certain backgrounds can render visualisation of fingerprint impression patterns very difficult, having the flexibility to judiciously tune the foreground colour of the fingerprint impression patterns is a significant advantage (Continued)

since it permits instantaneous improvements in visualisation without needing to resort to using a different fingerprint powder. The invention also relates inter alia to corresponding methods and specialised apparatus for fingerprinting.

36 Claims, 6 Drawing Sheets

(51) Int. Cl.
    *G06K 9/00*     (2006.01)
    *A61B 5/1171*     (2016.01)

(58) Field of Classification Search
    USPC .......................................................... 382/124
    See application file for complete search history.

(56) References Cited

U.S. PATENT DOCUMENTS

| | | | |
|---|---|---|---|
| 2012/0178099 A1 | 7/2012 | Jana et al. | |
| 2013/0149428 A1* | 6/2013 | Pitts ..................... | A61B 5/1172 427/1 |

* cited by examiner

Figure 5.1

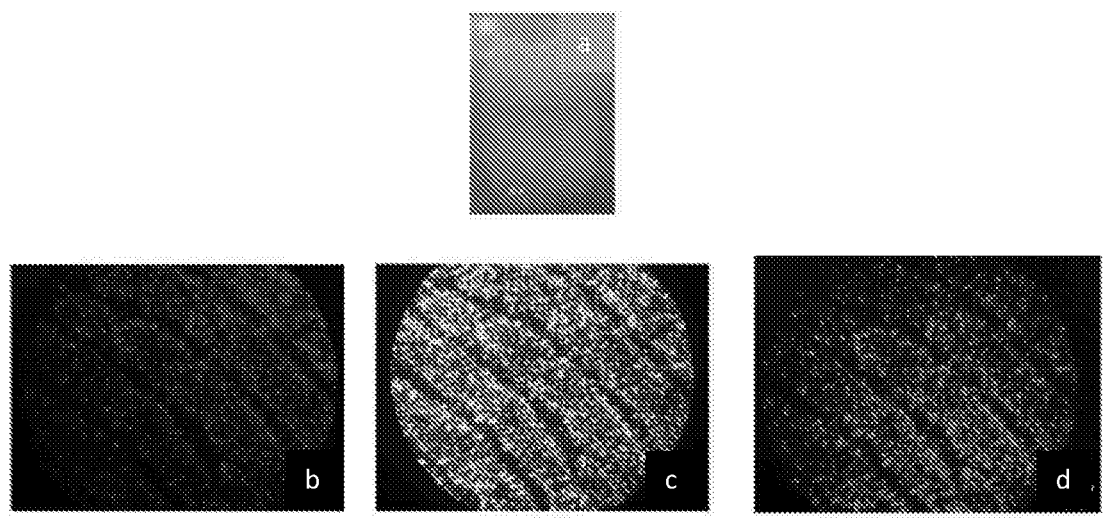
Figure 9
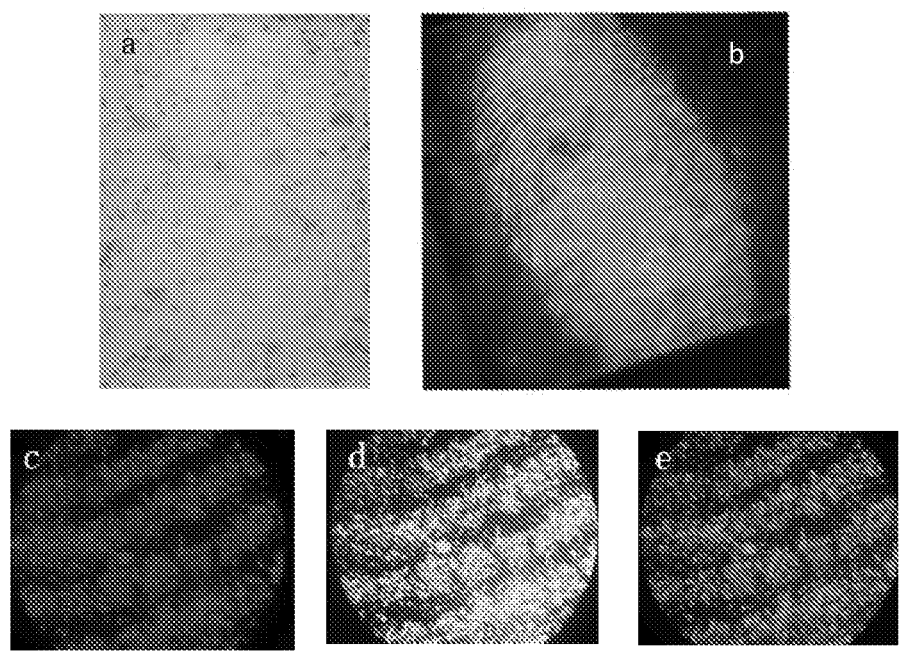
Figure 9.1

METHOD OF FINGERPRINTING WITH USING CARBOGENIC NANOPARTICLE

RELATED APPLICATIONS

This application is a national stage entry under 35 U.S.C. § 371 of International Patent Application No. PCT/GB15/052698, filed Sep. 18, 2015, which claims the benefit of and priority to GB 1416602, filed Sep. 19, 2014, the contents of which are hereby incorporated by reference in their entireties.

INTRODUCTION

The present invention relates to a fingerprint powder composition for the visualisation of latent fingerprints. The invention also relates to inter alia a use of particular nanoparticles in fingerprinting, methods of preparing the fingerprint composition and component(s) thereof, a method of fingerprinting, an imagable impression pattern or a tape-lifted imagable impression pattern, a method of imaging (including computer-implemented methods, corresponding apparatus, and relevant computer software), an imaged impression pattern, a database, and a fingerprint kit.

BACKGROUND

Fingerprinting continues to be the principle means by which police agencies identify criminals and solve crimes. The characteristic ridge patterns (minutiae) upon the palmar surfaces of hands and feet, especially upon finger tips, differentiate one human being from another, since generally speaking no two people have the exact same minutiae/ridge patterns.

Impressions of these unique ridge patterns are inevitably left behind when a person touches a surface with their finger, since natural secretions (e.g. sweat, natural oils, etc.) residing on the friction ridges of the finger will deposit fingerprint residues in a characteristic ridge pattern upon the surface. Police agencies can capitalise upon these deposits (latent fingerprints), and the uniqueness of each characteristic pattern, by "dusting for fingerprints" at a crime scene. This typically involves applying a 'developer' (e.g. with a fingerprint brush), typically a fingerprint powder, to a surface comprising or suspected of comprising a latent fingerprint, in order to enhance the contrast between the ridge pattern left by the fingerprint residues and the surface itself. Usually, once the 'developer' has been applied to the surface any excess powder is blown away to leave an imagable fingerprint impression pattern (corresponding to the minutiae of the latent fingerprint) which can either be directly imaged (e.g. through the taking of a photograph) and/or tape-lifted (i.e. by extracting the imagable fingerprint impression pattern from the surface with adhesive tape so that the pattern then resides on the adhesive of the tape) for later use/analysis. The imaged fingerprint can then be either compared to fingerprints in a fingerprint database and/or kept on record to facilitate identification of criminals or other persons who may have touched the surface which has been "dusted for fingerprints".

Currently a wide variety of fingerprint powders (developers) are available for use in fingerprinting. For instance, haddonite white, which is ideal when dusting for fingerprints on dark surfaces, contains titanium dioxide, kaolin, and French chalk, whilst dactyl black, which is more suitably for light surfaces, contains a combination of graphite, lamp-black, and gum acacia.

Often a particular fingerprint powder will be chosen to complement the surface in question. For instance, a dark coloured fingerprint powder is often employed for developing fingerprint patterns upon a light surface, and vice versa. An inherent problem exists in that different fingerprint powders must be used for different background surfaces in order to achieve optimal contrast between the fingerprint pattern and the background, since each individual fingerprint powder is generally tailored to complement certain qualities of the background. This requires a forensic investigator to be either equipped with multiple different types of fingerprint powders, which is highly inconvenient and fingerprinting opportunities may be scuppered if the forensic investigator "dusts" with the wrong type of fingerprint powder, or to compromise on image quality.

It is thus an object of the invention to solve one of the problems inherent with the prior art.

Another object of the invention is to provide a single fingerprint powder which may be appropriate for use on a variety of (radically) different background surfaces.

SUMMARY OF THE INVENTION

According to a first aspect of the present invention there is provided a fingerprint powder composition (FPC) comprising carbogenic nanoparticles (CNPs) and a diluent.

According to a further aspect of the present invention there is provided a kits of parts comprising a fingerprint powder (FP) and carbogenic nanoparticles.

According to a further aspect of the present invention there is provided a method of preparing a fingerprint powder composition, the method comprising forming a blend of carbogenic nanoparticles and a diluent.

According to a further aspect of the present invention there is provided a method of preparing a fingerprint powder composition, the method comprising providing carbogenic nanoparticles (e.g. as pre-formed carbongenic nanoparticles) and blending the carbogenic nanoparticles with a diluent.

According to a further aspect of the present invention there is provided a method of preparing a fingerprint powder composition, the method comprising forming carbogenic nanoparticles in situ within a diluent and/or with non-carbogenic nanoparticles, and optionally thereafter blending the carbogenic nanoparticles with a diluent and/or further diluent.

According to a further aspect of the present invention there is provided a method of preparing a fingerprint powder composition, the method comprising providing carbogenic nanoparticles (e.g. as pre-formed carbongenic nanoparticles and/or as carbogenic nanoparticles formed in situ within a diluent and/or with non-carbogenic nanoparticles) and optionally (suitably where necessary or desired, e.g. if CNPs formed in situ are not yet mixed with sufficient diluents) blending the carbogenic nanoparticles with a diluent (or further diluent).

According to a further aspect of the present invention there is provided a fingerprint powder composition (FPC) obtainable by, obtained by, or directly obtained by a method of preparing a fingerprint powder composition as defined herein.

According to a further aspect of the present invention there is provided a use of carbogenic nanoparticles in fingerprinting.

According to a further aspect of the present invention there is provided a use of carbogenic nanoparticles to facilitate visualisation of an imagable impression pattern (suitably an imagable impression pattern of a latent fingerprint).

According to a further aspect of the present invention there is provided a method of fingerprinting (or method of visualising or dusting for fingerprints), the method comprising:

i) coating a surface, comprising or suspected of comprising a latent fingerprint, with a fingerprint powder composition as defined herein;

ii) developing/providing an imagable impression pattern of the latent fingerprint within or from the coating of fingerprint powder composition;

iii) optionally tape-lifting said imagable impression pattern of the latent fingerprint from the surface;

iv) optionally imaging (e.g. photographing) the imagable impression pattern of the latent fingerprint.

According to a further aspect of the present invention, there is provided an imagable impression pattern or a tape-lifted imagable impression pattern obtainable by, obtained by, or directly obtained by the method of fingerprinting (or method of visualising or dusting for fingerprints) as defined herein.

According to a further aspect of the present invention there is provided a fingerprint imaging apparatus for imaging an imagable impression pattern, as defined herein, upon a background surface, the apparatus comprising:

(a) a variable (or tunable) wavelength radiation source operable to emit incident radiation at one or more (manually and/or automatically) selectable wavelengths (or incident radiation having a manually and/or automatically selectable distribution/intensity of wavelength(s)) to thereby expose the imagable impression pattern to incident radiation;

(b) an imaging device operable to capture an image of the imagable impression pattern during its exposure to the incident radiation (preferably incident radiation of a wavelength(s) or a distribution/intensity thereof which enables visualisation of the imagable impression pattern, e.g. a camera); and (c) an image storage medium for storing an image captured by the imaging device;

wherein the apparatus is optionally operable to capture multiple images of the imagable impression pattern, optionally during its exposure to different wavelengths of incident radiation (or incident radiation having different distributions/intensities of wavelength(s)).

According to a further aspect of the present invention there is provided a method of imaging an imagable impression pattern (or method of imaging fingerprints), as defined herein, upon a background surface, the method comprising:

(a) Exposing the imagable impression pattern to incident radiation at one or more (manually and/or automatically) selected wavelengths (or incident radiation having a manually and/or automatically selected distribution/intensity of wavelength(s));

(b) Tuning (or altering the selection of) the wavelength(s) of the incident radiation (suitably for optimal visualisation of the imagable impression pattern against the background surface);

(c) capturing an image of (or otherwise imaging) the imagable impression pattern during its exposure to the incident radiation (preferably incident radiation of a wavelength(s), and/or distribution/intensity thereof, which enables visualisation of the imagable impression pattern, e.g. a camera); and (d) storing the captured image;

wherein steps (a) and (b) may be performed in any order and optionally repeated one or more times;

wherein steps (a) to (d) may be repeated one or more times to generate multiple images of the imagable impression pattern during its exposure to different wavelengths of incident radiation (and/or different distributions/intensities of wavelengths).

According to a further aspect of the present invention there is provided a fingerprint imaging apparatus for imaging an imagable impression pattern, as defined herein, upon a background surface, the apparatus comprising:

(a) a variable (or tunable) wavelength radiation source operable to emit incident radiation at one or more (manually and/or automatically) selectable wavelengths to thereby expose the imagable impression pattern to incident radiation;

(b) an imaging device operable to capture an image of the imagable impression pattern during its exposure to the incident radiation (preferably incident radiation of a wavelength(s) which enables visualisation of the imagable impression pattern, e.g. a camera); and (c) an image storage medium for storing an image captured by the imaging device;

(d) (optionally) a background surface analyser operable to analyse the background surface and, on the basis of the analysis of the background surface, select one or more suitable wavelengths for the incident radiation (i.e. tune the incident radiation), wherein the background surface analyser comprises:

i. a background surface detector (which is optionally the same as the imaging device) configured or operable to obtain background surface information (and suitably convey said information to a computer); and ii. a computer configured or operable to analyse the background surface information obtained by the background detector and, on the basis of the analysis of the background surface information, select one or more suitable wavelengths for the incident radiation;

wherein the apparatus is optionally operable to capture multiple images of the imagable impression pattern, optionally during its exposure to different wavelengths of incident radiation.

According to a further aspect of the present invention there is provided a (optionally computer-implemented) method of imaging an imagable impression pattern (or an optionally computer-implemented method of imaging fingerprints), as defined herein, upon a background surface, the method comprising:

(a) Exposing the imagable impression pattern to incident radiation at one or more (suitably automatically) selected wavelengths;

(b) (optionally) operating a computer running pursuant to background surface analysis software (and optionally also to one or more databases) to:

i. obtain background surface information via a background surface detector (which is optionally the same as the imaging device);

ii. analyse the background surface information (optionally comparatively against the imagable impression pattern, be it an exposed or unexposed imagable impression pattern); and iii. on the basis of the analysis of the background surface information, automatically select (or tune) one or more suitable wavelengths for the incident radiation (suitably for optimal visualisation of the imagable impression pattern against the background surface);

(c) capturing an image of (or otherwise imaging) the imagable impression pattern during its exposure to the incident radiation (preferably incident radiation of a wavelength(s) which enables visualisation of the imagable impression pattern, e.g. a camera); and (d) storing the captured image;

wherein steps (a) and (b) may be performed in any order and optionally repeated one or more times (e.g. until visualisation of the imagable impression pattern against the background surface is optimised);

wherein steps (a) to (d) may be repeated one or more times to generate multiple images of the imagable impression pattern during its exposure to different wavelengths of incident radiation.

According to a further aspect of the present invention there is provided a use of a fingerprint imaging apparatus as defined herein in fingerprinting (or in imaging an imagable impression pattern as defined herein).

According to a further aspect of the present invention, there is provided a computer program, comprising software code for performing the computer-implemented method of imaging an imagable impression pattern defined herein when the computer program is run on a computer.

According to a further aspect of the present invention, there is provided a computer-readable medium comprising software code executable to cause a computer to perform the computer-implemented method of imaging an imagable impression pattern defined herein when the software code is executed on a computer.

According to a further aspect of the present invention, there is provided an imaged impression pattern (e.g. a photograph) of the latent fingerprint obtainable by, obtained by, or directly obtained by the method of fingerprinting (or method of visualising or dusting for fingerprints) as defined herein.

According to a further aspect of the present invention, there is provided an imaged impression pattern (e.g. a photograph) of the latent fingerprint, comprising an image of a pattern created by the fingerprint powder composition (or a developed or imaged derivative thereof) as defined herein.

According to a further aspect of the present invention, there is provided a method of fingerprint matching (or identifying a fingerprint), the method comprising comparing an imaged impression pattern as defined herein with one or more comparative fingerprint images.

According to a further aspect of the present invention, there is provided an image database comprising two or more imaged impression patterns of latent fingerprints as defined herein.

According to a further aspect of the present invention, there is provided a fingerprint kit (kit of parts) comprising a fingerprint powder composition as defined herein, and one or more items selected from:

i) One or more further fingerprint powders (e.g. one or more colours thereof);
ii) One or more magnetic powders (e.g. one or more colours thereof);
iii) One or more fluorescent powders (e.g. one or more colours thereof);
iv) Fingerprint lifting tape (suitably transparent);
v) One or more fingerprint lifting cards;
vi) Cutting device (e.g. scalpel, scissors);
vii) One or more fingerprint brushes;
viii) One or more magnetic applicators;
ix) Imaging apparatus (e.g. UV lamp and/or a camera or other suitable imaging device).

Alternative aspects of the invention may be essentially identical to any of the aforementioned aspects except that, rather than relating to a fingerprint powder composition they may instead relate to any powder composition (e.g. powder coating composition, suitably wherein the diluent and/or one or more other components of the powder composition facilitates binding to a particular surface, e.g. a pretreated surface). Likewise, methods, apparatus, kits, and uses may be adapted accordingly to relate to powder compositions in general (e.g. methods of imaging powder compositions). For example, a positively-charged powder coating composition may be produced by methods well known in the art, and such a powder coating composition can be adhered to a plasma treated surface to form a powder coating that is suitably washproof albeit removable using scotch tape and such like.

Any features, including optional, suitable, and preferred features, described in relation to any particular aspect of the invention may also be features, including optional, suitable, and preferred features, of any other aspect of the present invention.

BRIEF DESCRIPTION OF THE DRAWINGS

For a better understanding of the invention, and to show how embodiments of the same are put into effect, reference is now made, by way of example, to the following diagrammatic drawings, in which:

FIG. 5.1 shows various photographs of an aC-dots (0.7 wt %)/silica-dusted fingerprint, including: a) a fingerprint deposited upon a soft drink bottle foil; b) the same fingerprint exposed under bright field illumination (poor contrast); (c) the same fingerprint exposed under fluorescence microscopy violet radiation (good contrast and facet resolution); d) the same fingerprint exposed under (e) the same fingerprint exposure under green light (only weak ridge patterns are visible); blue radiation (good contrast and facet resolution); and (e) the same fingerprint exposed under (e) the same fingerprint exposure under green light (only weak ridge patterns are visible); green light (only weak ridge patterns are visible).

FIG. 9 shows fluescence microscopy images of (I) Fingerprint deposited on a glass slide developed with 0.7 wt % aC-dots with fingerprint powder composition A5a (Instant White Fingerprint Powder (commercial powder)) (II-IV) fluorescence images under different wavelengths.

FIG. 9.1 shows a visualised fingerprint on a glass slide developed with uC-dots: (a) under UV light; and (b) with a fluorescent microscope (100× mag.) under violet, blue and green excitation wavelength, respectively (c, d and e).

FIG. 9.2 shows a comparison between fingerprints visualised at various wavelengths using either: a) the uC-dots powder (top row); and b) commercial fluorescent powders (bottom row).

DETAILED DESCRIPTION OF THE INVENTION

Definitions

Figure 1:
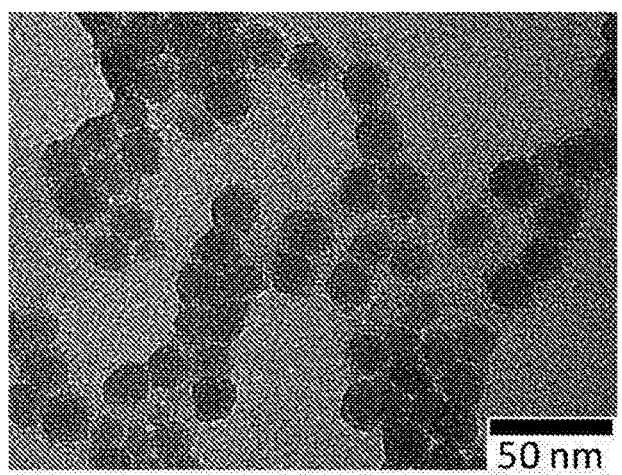
FIG. 1 shows a TEM image of aC-dots having a particle size between 15-25 nm.

Unless otherwise stated, the following terms used in the specification and claims have the following meanings set out below.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

For the avoidance of doubt, it is hereby stated that the information disclosed earlier in this specification under the heading "Background" is relevant to the invention and is to be read as part of the disclosure of the invention.

Unless stated otherwise, any reference herein to an "average" value is intended to relate to the mean value.

Where a composition is said to comprise a plurality of stipulated ingredients (optionally in stipulated amounts of concentrations), said composition may optionally include additional ingredients other than those stipulated. However, in certain embodiments, a composition said to comprise a plurality of stipulated ingredients may in fact consist essentially of or consist of all the stipulated ingredients.

Herein, where a composition is said to "consists essentially of" a particular component, said composition suitably comprises at least 70 wt % of said component, suitably at least 90 wt % thereof, suitably at least 95 wt % thereof, most suitably at least 99 wt % thereof. Suitably, a composition said to "consist essentially of" a particular component consists of said component save for one or more trace impurities.

Where the quantity or concentration of a particular component of a given composition is specified as a weight percentage (wt % or % w/w), said weight percentage refers to the percentage of said component by weight relative to the total weight of the composition as a whole. It will be understood by those skilled in the art that the sum of weight percentages of all components of a composition will total 100 wt %. However, where not all components are listed (e.g. where compositions are said to "comprise" one or more particular components), the weight percentage balance may optionally be made up to 100 wt % by unspecified ingredients (e.g. a diluent, such as water, or other non-essentially but suitable additives).

Herein, unless stated otherwise, the term "parts" (e.g. parts by weight, pbw) when used in relation to multiple ingredients/components, refers to relative ratios between said multiple ingredients/components. Expressing molar or weight ratios of two, three or more components gives rise to the same effect (e.g. a molar ratio of x, y, and z is x1:y1:z1 respectively, or a range x1-x2:y1-y2:z1-z2). Though in many embodiments the amounts of individual components within a composition may be given as a "wt %" value, in alternative embodiments any or all such wt % values may be converted to parts by weight (or relative ratios) to define a multi-component composition. This is so because the relative ratios between components is often more important than the absolute concentrations thereof in the liquid pharmaceutical compositions of the invention. Where a composition comprising multiple ingredients is described in terms of parts by weight alone (i.e. to indicate only relative ratios of ingredients), it is not necessary to stipulate the absolute amounts or concentrations of said ingredients (whether in toto or individually) because the advantages of the invention can stem from the relative ratios of the respective ingredients rather than their absolute quantities or concentrations. However, in certain embodiments, such compositions consists essentially of or consist of the stipulated ingredients and a diluents (e.g. water).

The term "mole percent" (i.e. mol %) is well understood by those skilled in the art, and the mol % of a particular constituent means the amount of the particular constituent (expressed in moles) divided by the total amount of all constituents (including the particular constituent) converted into a percentage (i.e. by multiplying by 100). The concept of mol % is directly related to mole fraction.

The term "substantially free", when used in relation to a given component of a composition (e.g. "a liquid pharmaceutical composition substantially free of compound X"), refers to a composition to which essentially none of said component has been added. When a composition is "substantially free" of a given component, said composition suitably comprises no more than 0.001 wt % of said component, suitably no more than 0.0001 wt % of said component, suitably no more than 0.00001 wt %, suitably no more than 0.000001 wt %, suitably no more than 0.0000001 wt % thereof, most suitably no more than 0.0001 parts per billion (by weight).

The term "entirely free", when used in relation to a given component of a composition (e.g. "a liquid pharmaceutical composition entirely free of compound X"), refers to a composition containing none of said component.

Suitably, unless stated otherwise, where reference is made to a parameter (e.g. pH, pKa, etc.) or state of a material (e.g. liquid, gas, etc.) which may depend on pressure and/or temperature, suitably in the absence of further clarification such a reference refers to said parameter at standard ambient temperature and pressure (SATP). SATP is a temperature of 298.15 K (25° C., 77° F.) and an absolute pressure of 100 kPa (14.504 psi, 0.987 atm).

Herein, the term "particle size" or "pore size" refers respectively to the length of the longest dimension of a given particle or pore. Particle and pore sizes may be measured using methods well known in the art, including a laser particle size analyser and/or electron microscopes (e.g. transmission electron microscope, TEM, or scanning electron microscope, SEM).

Herein, the term "nanoparticles" refers to particles having a particle size (or average particle size) of less than or equal to 100 nm.

Herein, the term "fingerprinting" (also known as "fingerprint development" or "dusting for fingerprints") refers to a well-known process in which "latent fingerprints" (which are, strictly speaking, impressions of finger prints left on a surface that has been touched), which may optionally be invisible or scarcely visible to the naked eye, are rendered more visible. The process typically involves the use of a "developer" (i.e. fingerprint powder or fingerprint powder composition), suitably a powder that may be applied to latent fingerprints on a surface to impart visual contrast between the ridge patterns (or "minutiae") and the surface upon which the latent fingerprint lie.

Herein, the term "latent fingerprint" refers to an undeveloped pattern of fingerprint residues upon a surface, which typically represents an impression of a corresponding fingerprint left behind after said surface has been touched by a finger. The fingerprint residues typically comprise natural secretions which become deposited upon a surface in a pattern characteristic of an impression of the "friction ridges" of the finger which touched the surface.

Herein, where a composition is said to "consists essentially of" a particular component, said composition suitably comprises at least 70 wt % of said component, suitably at least 90 wt % thereof, suitably at least 95 wt % thereof, most suitably at least 99 wt % thereof. Suitably, a composition said to "consist essentially of" a particular component consists of said component save for one or more trace impurities.

General Methodology and Advantages of the Invention

The fingerprint powder compositions of the invention are, as per existing fingerprint powders, suitable for facilitating visualisation of latent fingerprints, whether at a crime scene or elsewhere. As per usual, such visualisation generally involves initial "dusting for fingerprints" through the application of the fingerprint powder to a surface comprising or suspected of comprising latent fingerprings to thereby produce a fingerprint impression pattern, and subsequent visualisation with the naked eye and/or with an imaging/image-capture device. However, the benefits of the invention are realised when the relevant fingerprint impression pattern (formed using the fingerprint powder compositions of the invention) is visualised whilst being exposed to incident/input radiation from a radiation source.

The fingerprint powder compositions of the invention contain carbogenic nanoparticles (CNPs), whose excitation-dependent emission properties enable a forensic investigator to readily visualise (whether with the naked eye or an imaging/image-capture device) latent fingerprints in a variety of different colours by simply adjusting the wavelength (s) (or wavelength distributions) of incident radiation to which the latent fingerprings are exposed. This colour-tunability offers significant advantages. For example, the output colour (or output wavelength, since the invention is not necessarily restricted to only visible light outputs) emitted by the fingerprint powder composition on exposure to particular input wavelengths (from the radiation source) can be judiciously tuned for a given background (which may be coloured, patterned, or textured so as to render visualisation difficult with certain fingerprint powders) so as to optimise visibility and/or contrast of the fingerprint impression pattern against a particular background. The same fingerprint powder composition may be used to visualise latent fingerprints on a radically different background (where the initial visualisation colour would be unsuitable) by simply adjusting the input wavelength(s)—there is no need for a forensic investigator to carry or use multiple different fingerprint powders to accommodate a variety of different backgrounds.

As such, the fingerprint powder compositions of the invention allow the forensic investigator to "dust for fingerprints" on a variety of radically different backgrounds with just a single fingerprint powder, thereby avoiding the inconvenience of carrying multiple different types of fingerprint powders or the compromising required if only a single traditional fingerprint powder is used.

Another advantage is that the above-mentioned benefits can be achieved without imparting toxic properties to a fingerprint powder (e.g. as may otherwise be the case if heavy metal-based quantum dots were used instead).

Overall, the invention provides a simple, convenient, inexpensive, and versatile solution to the problems inherent with the prior art, and furthermore facilitates the use of complementary automated equipment which makes the forensic investigator's job much easier.

The benefits of the invention may be realised in fields beyond forensics and, as such, the invention also provides a powder composition (not necessarily limited to the field of fingerprinting) comprising carbogenic nanoparticles (CNPs) and a diluents, where all features relating to the fingerprint powder compositions defined herein may be equally applied to said general powder compositions. Likewise, all kits, methods, uses, imagable impression patterns, imaging apparatuses, computer software, etc. defined herein in relation to fingerprint powder compositions may be equally applicable or adapted to be applicable to general powder compositions. In certain embodiments, said powder compositions may be used in articles intended to exhibit different output emissions in response to different input radiation.

Fingerprint Powder Composition

The present invention provides a powder composition, suitably as defined herein. The powder composition is suitably a fingerprint powder composition. The powder composition suitably comprises carbogenic nanoparticles (CNPs) and a diluent. Suitably the powder composition may consist essentially of or even consist of CNPs and a diluent, though the diluent itself may be a diluent composition comprising one or more ingredients.

The powder composition suitably comprises at least 0.001 wt % carbogenic nanoparticles, suitably at least 0.01 wt %, suitably at least 0.1 wt %, suitably at least 0.5 wt %. The powder composition suitably comprises at most 20 wt % carbogenic nanoparticles, suitably at most 10 wt %, suitably at most 5 wt %, more suitably at most 2 wt %, most suitably at most 1 wt %. In a particular embodiment, the powder composition comprises about 0.7 wt % carbogenic nanoparticles.

The powder composition suitably comprises at least 80 wt % diluent, suitably at least 90 wt %, suitably at least 95 wt %, more suitably at least 98 wt %, most suitably at least 99 wt %. The powder composition suitably comprises at most 99.999 wt % diluent, suitably at most 99.99 wt %, suitably at most 99.9 wt %, suitably at most 99.5 wt %. In a particular embodiment, the powder composition comprises about 99.3 wt % diluent.

The powder composition suitably comprises the carbogenic nanoparticles and diluent in a respective weight ratio of between 0.001-20:99.999-80 (or 1:4-99999), suitably between 0.01-10:99.99-90 (or 1:9-9999), suitably between 0.1-5:99.9-95 (or 1:19-999), suitably between 0.1-2:99.9-98 (or 1:49-999), suitably between 0.5-1:99.5-99 (or 1:99-199).

The powder composition suitably yields (suitably consistent) output radiation of a given wavelength(s) (output wavelength(s)) in response to exposure to a given input radiation of a given wavelength(s) (input wavelength(s)). Suitably the, some, or all output wavelength(s) are different to the, some, or all input wavelength(s) (i.e. suitably the powder composition causes wavelength shifting when exposed to radiation or radiation within a certain range of wavelengths). Suitably, such wavelength shifting is the result of photoluminescence and/or scattering. The powder composition suitably exhibits photoluminescence—i.e. the emission of photons following the absorption of photons (electromagnetic radiation)—and/or scattering (e.g. Rayleigh scattering, Brillouin scattering). Most suitably the powder composition exhibits fluorescence.

The, some or all output wavelength(s) ($\lambda$) of radiation emitted by the powder compositions of the invention in response to their exposure to (and/or absorption of) input radiation of a given wavelength(s) (especially input radiation having wavelengths in the range of 1000 nm to 10 nm, suitably 700 nm to 100 nm, suitably 700 nm to 300 nm) is suitably in the range of the visible spectrum (e.g. within the range of about 390 to 700 nm). Suitably the the powder composition exhibits excitation-dependent emission (i.e. output radiation changed by changing the input radiation, especially the wavelengths), especially in response to input wavelength(s) greater than or equal to 100 nm, suitably greater than or equal to 200 nm, suitably greater than or equal to 300 nm.

The powder composition suitably exhibits a defined quantum yield ($\Phi$)—i.e. emits a given number of output photons per given number of input/incident photons (be these incident photons absorbed and/or scattered) at any given input wavelength(s) or across all measured wavelengths (though suitably wavelengths in the range of 1000 nm to 10 nm, suitably 700 nm to 100 nm, suitably 700 nm to 300 nm, suitably in respect of both input and output radiation)—or at least a defined average quantum yield—i.e. yields a given average number of output photons per average number of input photons at any given input wavelength(s) or across all measured wavelengths. Most suitably, references herein to a quantum yield (or maximum quantum yield), suitably means the quantum yield over all measured input/output wavelengths (though suitably wavelengths in the range of 1000 nm to 10 nm, suitably 700 nm to 100 nm, suitably 700 nm to 300 nm—though the input radiation may be different from the output radiation, especially in terms of wavelength and/or the distribution thereof, "quantum yield" suitably refers to yields of output photons/radiation within a stipulated wavelength range for a given quantum of input radiation, though suitably the input radiation in relation to which quantum yields are calculated are suitably also within the stipulated wavelength range). Quantum yield ($\Phi$) is a concept well understood in the art, and may be expressed, be it nominal or average, by the equation:

$$\Phi = \frac{\text{Number of photons emitted} + \text{scattered}}{\text{number of photons absorbed} + \text{incident photons}} \quad (1)$$

Methods of measuring quantum yields are well understood in the art.

The powder composition suitably exhibits a maximum quantum yield ($\Phi_{max}$—that being the maximum quantum yield achievable across all measured input/output wavelengths, though suitably across output wavelengths and preferably also input wavelengths in the range of 1000 nm to 10 nm, suitably 700 nm to 100 nm, suitably 700 nm to 300 nm), suitably a maximum quantum yield in respect of photons specifically within the visible spectrum (i.e. 390-700 nm), of at least 1% of that of anthracene at the same input wavelength ($\lambda_{ex}$), suitably at least 5%, more suitably at least 10%, more suitably at least 14%, suitably at most 30 wt %, more suitably at most 20 wt %, more suitably at most 16 wt %.

Above certain concentrations, carbogenic nanoparticles begin to "self-quench" and quantum yields will tend to decrease. Below certain concentrations, carbogenic nanoparticles may become insufficiently visible within the powder composition to be practical, even if the quantum yield is high for the given amount of carbogenic nanoparticles. Suitably the powder composition comprises a weight % of CNPs sufficient for the powder composition to exhibit a quantum yield (across the full wavelength range, suitably between 1000 nm to 10 nm for both input and output radiation) that is within +/−30% of the maximum quantum yield achievable over the whole range of wt % of CNPs (from 0-100 wt %), suitably within +/−10%, suitably within +/−5%, suitably within +/−1%. Suitably the powder composition comprises a weight % of CNPs sufficient for the powder composition to exhibit a quantum yield per weight % of CNPs (i.e. $\Phi$/wt % CNPs) that is within +/−30% of the maximum that is achievable over the whole range of wt % of CNPs (from 0-100 wt %), suitably within +/−10%, suitably within +/−5%, suitably within +/−1%.

In powder compositions of the invention, the carbogenic core (or carbogenic nature) of the CNPs is suitably primarily (preferably substantially exclusively) responsible for the quantum yield (suitably responsible for at least 50% of the quantum yield, more suitably at least 60% thereof, more suitably at least 70% thereof, more suitably at least 90% thereof, more suitably at least 99% thereof), suitably across all wavelengths or those mentioned herein, suitably as opposed to any chromaphore or fluorophore within the CNPs and/or diluent.

Suitably there are (substantially) no covalent bonds between the CNPs and diluent within the powder composition (that is notwithstanding the fact that CNPs may be carbogenically coated non-carbogenic nanoparticles, which are suitably not covalently linked to any uncoated non-carbogenic nanoparticles and/or other diluents).

Suitably, the CNPs are independent particles.

Suitably the powder composition is a blended mixture of particles (suitably a substantially uniform dispersion thereof), most suitably a solid blend. This may suitably include where the CNPs are pre-formed before being mixed with the diluent and/or where the CNPs are formed in situ within the diluent and/or with non-carbogenic nanoparticles before being subsequently mixed with a diluent (e.g. such as where diluent nanoparticles are carbogenically coated in situ). However, most suitably the blended mixture of particles is obtained by mixing pre-formed CNPs with the (pre-formed) diluent, optionally as a particulate dispersion or solution within a solvent (most suitably water—i.e. aqueous dispersion or solution) before the solvent is removed (e.g. via a freeze drying process).

Suitably the powder composition is substantially non-toxic. Suitably the powder composition is substantially (most preferably entirely) free of heavy metals (suitably whether the metals are in elemental form or a metal species as part of a compound). Suitably the powder composition is substantially (most preferably entirely) free of metals whose elemental form has a density above 7 g/cm$^3$, suitably above 6 g/cm$^3$, suitably above 3.5 g/cm$^3$. Suitably the powder composition is substantially (most preferably entirely) free of metals having an atomic weight greater than or equal to 40, suitably greater than or equal to 50, more suitably greater than or equal to 60, though suitably less than or equal to 92. Suitably the powder composition is substantially (most preferably entirely) free of metals in Groups 3 to 16 that are in periods 4 and greater. Most suitably, the powder composition is substantially (most preferably entirely) free of chromium, cobalt, nickel, copper, zinc, arsenic, selenium, silver, cadmium, antimony, mercury, thallium and lead.

Suitably the image resolution (upon imaging/visualisation) of powder compositions of the invention is substantially the same or greater than the image resolution of a corresponding powder composition without any CNPs.

Suitably the CNPs are physically and chemically inert within the powder composition, especially at 25° C.

Carbogenic Nanoparticles

The carbogenic nanoparticles are suitably nanoparticles comprising, consisting essentially of, or consisting of a carbonaceous (i.e. carbon-rich) material(s). It will be understood by the skilled person that references herein to a carbonaceous material(s) may include a mixture of such materials. Such nanoparticles may take a variety of forms and yet still be considered carbogenic nanoparticles.

In a particular embodiment, the carbogenic nanoparticles consist essentially of a carbonaceous material (suitably formed by carbonizing a carbogenic precursor(s)), and the nanoparticles themselves may each suitably have a substantially uniform composition.

In an alternative embodiment, the carbogenic nanoparticles may comprise a mixture of a carbonaceous material and a non-carbonaceous material. Suitably, in such embodiments, the carbogenic nanoparticles have a core comprising the non-carbonaceous material (e.g. this may be a diluent as defined herein, e.g. diluent nanoparticles, e.g. silica nanoparticles) and a coating upon the core comprising the carbonaceous material—e.g. carbogenically-coated non-carbogenic nanoparticles. Such nanoparticles may exhibit a core-shell structure. However, in some embodiments, the nanoparticles may be carbogenically-coated nanofibres. Regardless of the exact structure, such nanoparticles are only carbogenic nanoparticles if the particles themselves have a carbonaceous outer surface, since it is the interaction between incident radiation and such carbonaceous material which imbues the powder composition with the desired properties. In a particular embodiment, carbogenically-coated non-carbogenic nanoparticles comprise a silica core with a carbogenic coating.

In preferred embodiments, the carbogenic nanoparticles consist essentially of a carbonaceous material.

It will be appreciated by those skilled in the art that different types of CNPs may be used within the same powder composition. In preferred embodiments, the only CNPs contained by the powder composition are the carbogenic nanoparticles that consist essentially of a carbonaceous material.

The carbogenic nanoparticles suitably have a particle size (or average particle size) between 0.5 and 101 nm, more suitably between 1 and 50 nm, suitably between 10 and 40 nm, suitably between 14 and 31 nm.

The carbogenic nanoparticles are suitably (substantially) insoluble, suitably insoluble in water and/or hexane (i.e. have a solubility of less than or equal to 10 mg/L, suitably less than or equal to 1 mg/L, suitably less than or equal to 0.1 mg/L, suitably less than 0.01 mg/L).

Though the CNPs suitably impart photolumiscent and/or scattering properties to powder compositions of the invention, suitably the same CNPs (but in pure form) exhibit substantially no photolumiscent and/or scattering properties (or have quantum yields less than 0.1, suitably less than 0.01, more suitably less than 0.001, more suitably less than 0.0001) when exposed to an input radiation of the same wavelength which yields the highest quantum yield for the corresponding powder composition. It is believed that this is due to a self-quenching effect when the CNPs are too concentrated.

Carbogenic nanoparticles are notoriously difficult to characterise, and may be suitably defined by their method of production. However, carbogenic nanoparticles suitable for use with the invention may have any of the characteristic properties mentioned herein, and may alternatively or additionally be defined by reference to their carbon content and/or the carbon content of the carbonaceous material of which they are composed or part-composed.

The carbon content (e.g. as deduced by elemental analysis) (suitably by mass) of the carbonaceous material(s) of the CNPs is suitably greater than or equal to 40% C, suitably greater than or equal to 42% C, suitably greater than or equal to 43% C. The carbon content of the carbonaceous material(s) of the CNPs is suitably less than or equal to 60% C, suitably less than or equal to 50% C, suitably less than or equal to 49% C.

The carbon content (e.g. as deduced by elemental analysis) (suitably by mass) of the CNPs is suitably greater than or equal to 40% C, suitably greater than or equal to 42% C, suitably greater than or equal to 43% C. The carbon content of the CNPs is suitably less than or equal to 60% C, suitably less than or equal to 50% C, suitably less than or equal to 49% C.

The nitrogen content (e.g. as deduced by elemental analysis) (suitably by mass) of the carbonaceous material of the CNPs is suitably greater than or equal to 1% N, suitably greater than or equal to 3% N, suitably greater than or equal to 5% N, suitably greater than or equal to 6% N. The nitrogen content of the carbonaceous material of the CNPs is suitably less than or equal to 20% N, suitably less than or equal to 15% N, suitably less than or equal to 11% N.

The nitrogen content (e.g. as deduced by elemental analysis) (suitably by mass) of the CNPs is suitably greater than or equal to 1% N, suitably greater than or equal to 3% N, suitably greater than or equal to 5% N, suitably greater than or equal to 6% N. The nitrogen content of the CNPs is suitably less than or equal to 20% N, suitably less than or equal to 15% N, suitably less than or equal to 11% N.

Suitably the CNPs are formed by a method as defined herein, suitably using carbogenic precursor(s) (and optionally non-carbogenic precursor(s), for example, non-carbogenic nanoparticles for carbogenically coating) as described herein.

Though the carbogenic nanoparticles are suitably not (or are suitably free of) graphite and/or graphite particles (suitably the particles or at least the carbonaceous material thereof has a carbon content of less than or equal to 70% C), in a particular embodiment the carbogenic nanoparticles may in fact be or comprise graphitic or highly graphitic nanoparticles, and in a particular embodiment the carbogenic nanoparticles may in fact be or comprise amorphous graphite nanoparticles. Likewise, though the carbogenic nanoparticles are suitably not (or are suitably free of) graphene and/or diamonds particles (e.g. graphene dots and/or nano-diamonds), in a particular embodiment the carbogenic nanoparticles may in fact be or comprise graphene and/or diamonds nanoparticles.

Diluent

Any suitable diluent may be used within the powder compositions of the invention.

Suitably, the diluent allows (or causes) CNPs to exhibit the, some, or all of the effects mentioned herein (e.g. the capacity to emit different output radiation in response to a change in the input radiation, preferably with a wavelength shift between the input and output) when a part of the powder composition. Suitably the diluent promotes (or increases the level of) such effects, especially compared to undiluted CNPs (e.g. pure CNP powders).

Suitably, addition (and/or mixing in) of the diluent (e.g. suitably when a powder composition is produced having a CNPs/diluents weight ratio somewhere within the range of 1:4-199) to undiluted CNPs (suitably that otherwise emit substantially no output radiation in response to a given input radiation) transforms the emission properties (and/or photoluminescent and/or scattering properties) of the CNPs, suitably causing a relative increase in the maximum quantum yield ($\Phi_{max}$—that being the maximum quantum yield achievable across all input/output wavelengths, though suitably across output wavelengths and preferably also input wavelengths in the range of 1000 nm to 10 nm, suitably 700 nm to 100 nm, suitably 700 nm to 300 nm), suitably a maximum quantum yield in respect of photons specifically within the visible spectrum (i.e. 390-700 nm)—suitably the addition of such a diluent decreasing self-quenching between the CNPs to thereby allow emission of output radiation.

Moreover, addition (and/or mixing in) of the diluent (e.g. suitably when a powder composition is produced having a CNPs/diluents weight ratio somewhere within the range of 1:4-199) to undiluted CNPs (suitably that otherwise emit substantially no output radiation in response to a given input radiation) transforms the emission properties (and/or photoluminescent and/or scattering properties) of the CNPs, suitably causing the powder composition to exhibit excitation-dependent emission properties (at least within a certain range of input wavelengths).

The powder composition suitably comprises the CNPs and diluent in respective absolute weight concentrations and/or a relative weight ratio that produces a maximum quantum yield ($\Phi_{max}$—that being the maximum quantum yield achievable across all input/output wavelengths, though suitably across output wavelengths and preferably also input wavelengths in the range of 1000 nm to 10 nm, suitably 700 nm to 100 nm, suitably 700 nm to 300 nm) that is at least 50% of the highest possible maximum quantum yield (suitably the highest possible maximum quantum yield in respect of photons specifically within the visible spectrum, i.e. 390-700 nm) across all absolute weight concentrations and/or relative weight ratios, suitably at least 70% of the highest possible maximum quantum yield, suitably at least 80% of the highest possible maximum quantum yield, suitably at least 90% of the highest possible maximum quantum yield, suitably at least at least 95% of the highest possible maximum quantum yield. The respective absolute weight concentrations and/or relative weight ratio of CNPs and diluent that produce this highest possible maximum quantum yield may be collectively termed "ideal" and, as such, the powder composition suitably comprises the CNPs and diluent in respective absolute weight concentrations and/or a relative weight ratio that is at least 50% ideal, more suitably at least 70% ideal, more suitably at least 80% ideal, more suitably at least 90% ideal, more suitably at least 95% ideal. This can be readily extrapolated by those skilled in the art by preparing a number of sample powder compositions having a diverse range of absolute weight concentrations and/or relative weight ratios, and plotting their respective maximum quantum yields (obtainable via fluorescent spectroscopy or such like). The maximum quantum yield curve can then be extrapolated (either manually, automatically, and/or via a computer algorithm which generates a "line of best fit") to determine the highest possible maximum quantum yield and the respective absolute weight concentration and/or relative weight ratio of the CNPs and diluent at which this highest point occurs. In general, each CNPs/diluent combination will have a characteristic The diluent is suitably (substantially) inert, suitably especially in the presence of the CNPs.

The diluent is suitably stable to decomposition (i.e. yielding less than 0.1% decomposition whether by weight, moles, or other measurement), suitably especially in the presence of the CNPs.

The diluent is suitably stable to decomposition (i.e. yielding less than 0.1% decomposition whether by weight, moles, or other measurement) by input radiation (suitably with input wavelengths in the range of 1000 nm to 10 nm, suitably 700 nm to 100 nm, suitably 700 nm to 300 nm), suitably stable to decomposition when exposed to 240 kilojoules kJ of such radiation (equivalent to approximately 10 minutes direct irradiation with a 400 Watt W input radiation source, where there are no radiation losses/spillages), suitably stable to decomposition when exposed to 1.44 megajoules MJ of such radiation (equivalent to approximately 1 hour direct irradiation with a 400 Watt W input radiation source, where there are no radiation losses/spillages).

The diluent is suitably stable to decomposition (i.e. yielding less than 0.1% decomposition whether by weight, moles, or other measurement) by heat, suitably stable to decomposition when exposed to a temperature of 50° C. for 1 hours, suitably when exposed to a temperature of 100° C. for 1 hour.

The diluent is suitably incapable of photolumiscence within the visible spectrum, suitably incapable thereof regardless of the input radiation. The diluent suitably does not absorb any visible light. Suitably, if the diluent is capable of absorbing any visible light, the maximum quantum yield within the visible spectrum of the diluent per se (i.e. unmixed with CNPs) is at most 50% of that of the powder composition, suitably at most 30%, suitably at most 10%, suitably at most 5%, suitably at most 1%.

The diluent is suitably electrically non-conductive.

The diluent is suitably non-magnetic, suitably non-ferromagnetic and/or non-paramagnetic.

The diluent is suitably a solid, most suitably a particulate solid, such as a solid powder. Suitably the diluent comprises or consists essentially of solid particles having a particle size (or average particle size) of between 0.5 nm and 100 µm, suitably between 10 nm and 10 µm, suitably between 100 nm and 1 µm.

The diluent is suitably (substantially) insoluble in water and/or hexane (i.e. have a solubility of less than or equal to 10 mg/L, suitably less than or equal to 1 mg/L, suitably less than or equal to 0.1 mg/L, suitably less than 0.01 mg/L).

The carbon content (e.g. as deduced by elemental analysis) (suitably by mass) of the diluent is suitably less than or equal to 39% C, suitably greater than or equal to 30% C, suitably greater than or equal to 20% C, suitably greater than or equal to 5% C, suitably greater than or equal to 1% C, and is suitably free of carbon.

The nitrogen content (e.g. as deduced by elemental analysis) (suitably by mass) of the diluent is suitably less than or equal to 10% N, suitably less than or equal to 5% N, suitably less than or equal to 1% N, and is suitably free of nitrogen.

The diluent may in fact comprise one or more diluents, suitably as defined herein, though collectively they may constitute "the diluent".

The diluent suitably comprises one or more metal oxide-based and/or silicon oxide-based species, suitably in any protonation state (this may include silica, $SiO_2$ as well as silicates). In a particular embodiment, the diluent comprises or consists essentially of silica-based species comprising silica (e.g. silica or silicon dioxide) and/or one or more salts (e.g. silicates) thereof. In a particular embodiment, the diluent comprises or consists essentially of metal oxide-based species comprising one or more metal oxides (e.g. titania, $TiO_2$) and/or one or more salts (e.g. titanates) thereof. In a particular, the diluent comprises or consists essentially of both one or more silica-based species and/or one or more metal-oxide based species, suitably whether a blend of distinct compounds (e.g. silica mixed with titania) or whether a composite (e.g. aluminosilicates and derivatives thereof—e.g. clay). However, suitably the diluent is substantially (most preferably entirely) free of heavy metals (suitably whether the metals are in elemental form or a metal species as part of a compound). Suitably the diluent is substantially (most preferably entirely) free of metals whose elemental form has a density above 7 $g/cm^3$, suitably above 6 $g/cm^3$, suitably above 3.5 $g/cm^3$. Suitably the diluent is substantially (most preferably entirely) free of metals having an atomic weight greater than or equal to 40, suitably greater than or equal to 50, more suitably greater than or equal to 60, though suitably less than or equal to 92. Suitably the diluent is substantially (most preferably entirely) free of metals in Groups 3 to 16 that are in periods 4 and greater. Most suitably, the diluent is substantially (most preferably entirely) free of chromium, cobalt, nickel, copper, zinc, arsenic, selenium, silver, cadmium, antimony, mercury, thallium and lead.

The diluent is suitably free of carbonaceous and/or carbogenic material(s).

The diluent may in itself be or comprise a fingerprint powder (or at least may suitably serve as a fingerprint powder in its own right in the absence of CNPs), suitably any fingerprint powder (whether made of a single or multiple ingredients). As such, the diluent may comprise one or more of titanium dioxide, kaolin, French chalk, purified talc, kadin lenis, zinc sulphide, zinc oxide, barium sulphate, bismuth oxychloride, calcium carbonate, white tempura. Certain combinations of these ingredients may yield white fingerprint powders, such as titanium dioxide, kaolin and French chalk; titanium dioxide, purified talc and kadin lenis; zinc sulphide, zinc oxide, barium sulphate, titanium dioxide, bismuth oxychloride and calcium carbonate; titanium dioxide, white tempura or chalk.

Alternatively or additionally the diluent may comprise graphite, charcoal, lampblack, photocopier toners, anthrocene, gum acacia, powdered acacia, powdered resin of the Daemonorops draco plant. Certain combinations of these ingredients may yield black fingerprint powders, such as dactyl black, haddonite black, and dragon's blood.

Alternatively or additionally the diluent may comprise aluminium dust, fluorescent powders, magnetic powders, and lycopodium.

In a particular embodiment, the diluent comprises or consists essentially of silica, titania, clay, and/or a fingerprint powder.

In some embodiments, the diluent may be or comprise one or more of the carbogenic precursor(s) (and/or derivatives thereof—e.g. partially pyrolysed products). This allows CNP compositions, such as fingerprint powder compositions, to be formed in a more efficient manner—for example, the diluent may serve a dual function (diluent+carbogenic precursor(s)) to enable formation of CNPs in situ with said diluent, though the diluent may undergo some degree of change (e.g. partially react and/or partially pyrolyse) under the CNP-formation conditions, such that the ultimate diluent may comprise the excess carbogenic precursor/diluent, partially-reacted/partially-pyrolysed by-products of the carbogenic precursor, and/or mixture(s) thereof. By way of example, such CNP compositions may be formed from the carbogenic precursors citric acid and urea, where urea is present in excess so as to serve as a diluents. Pyrolysis of a mixture of said carbogenic precursors will produce a dilute CNP composition. A portion of the carbogenic precursor-based diluent (e.g. urea) reacts (e.g. with itself and/or citric acid) to produce CNPs, whilst the remainder of the carbogenic precursor-based diluent is either unreacted or partially-reacted carbogenic precursor which may then serve as a diluents. Excess and/or partially-reacted urea may then serve as the diluent.

The concentration of CNPs in a composition is readily discernable by techniques well known in the art. For example, calibrated standards may be used to determine CNP concentrations, for instance, to enable the relevant CNPs to be examined in isolation—e.g. with respect to their elemental analysis etc.

Method of Preparation a Fingerprint Powder Composition

The present invention provides a method of preparing a powder composition, suitably as defined herein.

Suitably a powder composition of the invention may be formed by providing carbogenic nanoparticles (e.g. whether as pre-formed carbogenic nanoparticles and/or as carbongenic nanoparticles formed in situ within a diluent and/or with non-carbogenic nanoparticles) and, where necessary or desired, blending the carbongenic nanoparticles with a diluent (or further diluent).

Suitably a powder composition of the invention may be formed by providing carbogenic nanoparticles (e.g. as pre-formed carbongenic nanoparticles) and blending the carbogenic nanoparticles with a diluent. Such a method is particularly suitable where the carbogenic nanoparticles are pre-formed, and suitably where the CNPs consist essentially of carbonaceous material. The method may involve simply blending respective powders (e.g. diluent and CNPs) (suitably to provide a substantially uniform blended powder mixture). Alternatively the method may involve pre-dispersing, pre-dissolve, and/or pre-suspending the respective powders (e.g. diluent and CNPs) within a solvent (most suitably water) and thereafter removing the solvent (e.g. in vacuo, most suitably by a freeze-drying or lyophilisation process) to yield a blended mixture (again which is suitably a substantially uniform blended powder mixture). Wet blending, followed by solvent removal (especially lyophilisation) has thus far been found to yield the best powder compositions, though the inventors have also found dry blending to yield excellent results.

Alternatively or additionally, a powder composition of the invention may be formed by generating carbogenic nanoparticles in situ with a diluent and/or with non-carbogenic nanoparticles and optionally thereafter (suitably where necessary or desired, e.g. if CNPs formed in situ are not yet mixed with sufficient diluent) blending the carbogenic nanoparticles with a diluent (or further diluent). This may simply involve mixing/blending a diluent with a carbogenic precursor(s) (e.g. such as a carbogenic precursor(s) that may be used to produce CNPs which consist essentially of carbonaceous material), optionally as above described, and thereafter forming the CNPs from the carbogenic precursor(s) in situ within the diluent. However, this alternative method is particularly suitable where the carbogenic nanoparticles in question are non-carbogenic nanoparticles coated with carbonaceous material (i.e. carbogenically coated non-carbogenic nanoparticles). Such methods may suitably involve coating or surface grafting non-carbogenic nanoparticles (be them diluent nanoparticles or otherwise) with a carbogenic precursor(s) to generate a coupled carbogenic precursor(s) (suitably comprising non-carbogenic nanoparticles attached to carbogenic precursor group(s)) and thereafter forming the CNPs (e.g. through carbonisation, e.g. by producing carbonaceous material upon the surface of the non-carbogenic nanoparticles). The method may involve pre-dispersing, pre-dissolve, and/or pre-suspending the diluent and/or non-carbogenic nanoparticles within a solvent (most suitably water), and reacting said diluent and/or non-carbogenic nanoparticles with a reactive carbogenic precursor(s) to produce a coupled carbogenic precursor(s). The solvent may thereafter be removed from the coupled carbogenic precursor (e.g. in vacuo, most suitably by a freeze-drying or lyophilisation process) before the coupled carbogenic precursor is then subjected to relevant conditions to yield carbogenically-coated non-carbogenic nanoparticles. The carbogenically-coated non-carbogenic nanoparticles may then be mixed and/or blended with a diluent (or further diluent) as aforedescribed.

Regardless of the specific method used, the relevant carbonaceous material (be it the carbogenic nanoparticles themselves, or a carbonaceous coating upon or around non-carbogenic nanoparticles) is suitably formed via carbonisation of one or more carbogenic precursors (which include carbogenic group(s), suitably organic compounds or organic groups comprising carbon and one or more other elements, such as hydrogen, oxygen, and/or nitrogen).

The carbonaceous material is suitably formed through the pyrolysis of the carbogenic precursor compound(s). Such pyrolysis suitably increases the % carbon content (suitably as measured by elemental analysis), though this is not always the case (e.g. where carbonization involves loss of some carbon-based by-products derived from the breakdown of the original carbogenic precursor compound(s), e.g. carbon monoxide or carbon dioxide).

Pyrolysis and carbonisation of carbogenic precursors is a complicated process, and both products and mechanisms are difficult to characterise. However, it is understood that many reactions take place during pyrolysis/carbonisation, including inter alia isomerisation, hydrogen transfer, dehydrogenation, condensation, decarboxylation, rearrangements, etc. The ultimate product (the carbogenic nanoparticles and/or carbonaceous material(s)) may be a varied mixture of carbogenic compounds.

Where the carbogenic nanoparticles are formed in situ within the diluent and/or with non-carbogenic nanoparticles, the carbogenic precursor(s) may be a compound (e.g. electrophile) or moiety (e.g. grafted carbogenic precursor group) that is grafted onto (or coupled with, suitably via chemical reaction) the surface of non-carbogenic nanoparticles (and/or diluent particles). Subsequent pyrolysis of the post-coupled product may then yield a carbonaceous surface coating around the non-carbogenic particles—they may then suitably be termed carbogenic nanoparticles in their own right, although they suitably have a non-carbogenic core but a carbogenic coating).

Providing/Preparing Carbogenic Nanoparticles

Suitably, carbogenic nanoparticles are formed through direct carbonisation of a suitable carbogenic precursor(s) and/or carbogenic precursor group(s). As described above, suitable carbogenic precursor(s) may include carbogenic precursor(s) and/or a coupled carbogenic precursor(s) (e.g. where carbon-based material is surface grafted to otherwise non-carbogenic nanoparticles).

In a particular embodiment, the carbogenic precursor(s) are free of nanoparticles having a non-carbogenic (or non-carbon-based core).

Suitably, carbogenic precursor(s) are pre-carbonized/pre-pyrolysed compound(s) (i.e. ones which have not been subjected to transformative heat), though in principle a carbogenic precursor(s) may be partially carbonised/pyrolysed. In such circumstances, however, a partially carbonised/pyrolysed material may still be extrapolated back to the original uncarbonised/unpyrolysed carbogenic precursor(s). Herein, unless stated otherwise, references to a carbogenic precursor(s) refer to original uncarbonised/unpyrolysed carbogenic precursor(s), though using partially carbonised materials to produce CNPs still falls within the scope of the present invention.

Suitably, the carbogenic precursor(s) used in the methods of the invention are suitable for forming a carbonaceous material, and are thus suitably carbonizable through pyrolysis. Suitably, the carbogenic precursor(s) comprise carbon, hydrogen, and optionally oxygen and/or nitrogen. Suitably, the carbogenic precursor(s) comprise at least carbon, hydrogen, and oxygen. Most suitably, the carbogenic precursor(s) comprise carbon, hydrogen, oxygen and nitrogen.

Suitably the carbogenic precursor(s) comprise a hydroxyl moiety (or a pyrolyically accessible form thereof—i.e. a derivative of hydroxyl or a group which, upon pyrolysis, readily produces a hydroxyl group, whether or not only transiently). Suitably the carbogenic precursor(s) comprise a carboxylic acid moiety or salt thereof (or a pyrolyically accessible form thereof—i.e. a derivative of a carboxylic acid, such as an ester, or a group which, upon pyrolysis, readily produces a carboxylic acid group, whether or not only transiently). Suitably the carbogenic precursor(s) comprise an amino moiety, an amine, or a salt thereof (e.g.

—NR$_a$R$_b$, e.g. wherein R$_a$ and R$_b$ are independently hydrogen or another suitably group such as optionally substituted (1-6C)alkyl, e.g. NH$_2$) optionally bonded to any other moiety (e.g. carbonyl, to produce an amide). Most suitably, the carbogenic precursor(s) comprise —OH, CO$_2$H, and NH$_2$ moieties or a suitably salt and/or derivative thereof.

The carbogenic precursor(s) may comprise more than one carbogenic precursor. For instance, in a particular embodiment, the carbogenic precursor(s) are citric acid (or a salt and/or a suitable derivative thereof, such as an tri-ester) and ethanolamine. Suitably the carbogenic precursor(s) comprise ethanolamine and citric acid in a molar ratio of between 1:1 and 5:1, suitably about 3:1. Suitably, during pyrolysis the citric acid and ethanolamine condense to yield 2-hydroxy-N1,N2,N3-tris(2-hydroxyethyl)propane-1,2,3-tricarboxamide, even if only transiently en route to polymerised and/or carbonized products. However, the carbogenic precursor(s) may be the condensation product of 3 moles of ethanolamine to 1 mole of citric acid (i.e. 2-hydroxy-N1,N2,N3-tris(2-hydroxyethyl)propane-1,2,3-tricarboxamide).

In an embodiment, at least one of the carbogenic precursor(s) is also a diluent (e.g. especially when present in excess), for instance, so that pyrolysis can deliver diluted CNPs directly without necessarily requiring a post-dilution step involving mixing of CNPs with a diluent. For instance, the carbogenic precursors citric acid and urea, where urea is present in excess so as to serve as a diluents, may be pyrolysed to produce CNPs in situ. Excess and/or partially-reacted urea may then serve as the diluent. By way of example, where two or more carbogenic precursor(s) are present with one serving as a diluent, the respective weight ratio of non-diluent carbogenic precursor(s) to diluent carbogenic precursor(s) is suitably between 1:2 and 1:10000, suitably between 1:5 and 1:1000, suitably between 1:10 and 1:200. Under such circumstances, under pyrolytic conditions (i.e. at high temperatures) the diluent need not be inert (especially vis a vis any other carbogenic precursor(s) present)

In another embodiment, the carbogenic precursor(s) may be a complex mixture of carbon-based materials. For instance, the carbogenic precursor(s) may comprise biomass or carbogenic precursor(s) extracted from biomass. In a particular embodiment, the carbogenic precursor(s) comprise plant material, for example, grass.

In embodiments where the carbogenic precursor(s) are coupled carbogenic precursor(s) with carbon-based material surface grafted to otherwise non-carbogenic nanoparticles, the coupled carbogenic precursor(s) is suitably formed by the reaction of a reactive carbogenic precursor group(s) with the non-carbogenic nanoparticles. This reaction suitably yields a coupled carbogenic precursor(s) comprising a non-carbogenic nanoparticle core with surface-grafted carbogenic precursor group(s). By way of example, the reactive carbogenic precursor group(s) may be a reactive silane (optionally with a displaceable leaving group or with a nucleophilically reactive group), such as (3-aminopropyl) triethoxy silane, and the non-carbogenic nanoparticles may be silica nanoparticles. The reaction to couple the carbogenic precursor(s) groups with the non-carbogenic nanoparticles may be facilitated by methods well known in the art, such as the application of heat and/or the use of a reaction solvent and/or other suitable reagents that may facilitate coupling. In an embodiment, an aqueous dispersion of silica is reacted with (3-aminopropyl)triethoxysilane at elevated temperatures (e.g. about 70° C.) before the coupled carbogenic precursor(s) is then purified. The coupled carbogenic precursor(s) may then be suitably carbonised through pyrolytic methods as defined herein.

Once prepared, the relevant carbogenic precursor(s) are suitably subjected to pyrolysis at elevated temperature, suitably for a period of time sufficient for the pyrolysis to proceed (substantially) to completion (or within 10% thereof) at the given temperature (e.g. 10 mins-5 hours, suitably at least 25 mins, suitably at most 3 hours; completion may be discernable by a number of analytical methods known in the art, including those disclosed in one of the Krysmann et al papers referenced in the Example section, though it may suitably involve observing substantially no further change in the fluorescence spectra or elemental analysis of a given diluted sample of the pyrolysed material). The pyrolysis suitably involves heating the relevant carbogenic precursor(s) at elevated temperatures, suitably to a temperature exceeding 100° C., suitably exceeding 150° C., suitably exceeding 180° C. The pyrolysis suitably involves heating the relevant carbogenic precursor(s) at elevated temperatures, suitably to a temperature not exceeding 500° C., suitably not exceeding 400° C., suitably not exceeding 320° C., suitably not exceeding 250° C.

In a particular embodiment (especially where CNPs are formed directly from carbon-based carbogenic precursor(s), for example, citric acid and ethanolamine), the pyrolysis involves heating the relevant carbogenic precursor(s) at a temperature between 210 and 250° C. for an appropriate period of time.

In a particular embodiment (especially where CNPs are formed directly from biomass, including plant-based material such as grass), the pyrolysis involves heating the relevant carbogenic precursor(s) at a temperature between 280 and 320° C. for an appropriate period of time.

In a particular embodiment (especially where CNPs are formed directly from coupled carbogenic precursor(s), for example, the silica nanoparticles with surface-grafted carbogenic precursor group(s)), the pyrolysis involves heating the relevant carbogenic precursor(s) at a temperature between 280 and 320° C. for an appropriate period of time.

In a particular embodiment, (especially where CNPs are formed in situ within a diluent which itself is or comprises one or more carbogenic precursors, for example, citric acid with an excess of urea), the pyrolysis involves heating the relevant carbogenic precursor(s) at a temperature between 210 and 250° C. for an appropriate period of time.

In general, pyrolysis involves heating at temperatures above 180° C., suitably above 200° C., suitably above 220° C., for a period suitable to achieve complete pyrolysis at the relevant temperature. Heating at temperatures below these levels may not enable sufficient carbonization to occur.

However, pyrolysis may be performed in stages. For instance, the relevant carbogenic precursor(s) may be heated at a first pyrolysis temperature (e.g. between 150 and 200° C., suitably between 170 and 190° C., suitably at about 180° C.) for a first period of time (e.g. approximately 30 mins or until pyrolysis at this temperature is substantially complete); and thereafter heated at a second pyrolysis temperature (e.g. between 200 and 350° C., suitably between 220 and 240° C., suitably at about 230° C.) for a second period of time (e.g. approximately 30 mins or until pyrolysis at this temperature is substantially complete); and optionally thereafter further heated at a third pyrolysis temperature (e.g. between 250 and 400° C., suitably between 290 and 310° C., suitably at about 300° C.) for a third period of time (e.g. approximately 30 mins or until pyrolysis at this temperature is substantially complete). At any stage a sample of the pyrolysis mixture may be analysed to determine whether the pyrolysis is suitably complete for a sufficient pyrolysis temperature.

After pyrolysis is complete, the resulting carbonized materials (suitably now CNPs) are suitably purified. Purification of the CNPs suitably involves one or more of:

- Forming a dispersion of the CNPs within a solvent (e.g. water), suitably in a solvent within which the CNPs are (substantially) insoluble as defined herein;
- Filtering the dispersion (e.g. to remove impurities that dissolve in the solvent);
- Dialysing the dispersion (e.g. using an appropriate dialysis membrane or tubing membrane), suitably at a molecular weight cut off of at least 500 Daltons (Da), suitably at least 1000 Da, suitably at least 3000 Da, suitably at about 3500 Da, suitably for a time sufficient to remove (substantially) all impurities and/or by-products having a molecular weight below the cut off;
- Refluxing in acid (e.g. 3M $HNO_3$);
- Centrifuging to remove large particles.

The most relevant purification steps which generally apply to all syntheses are forming a dispersion of the CNPs (generally an aqueous dispersion) and dialysing the dispersion.

Though in most embodiments, purification takes place after the CNPs have been formed, in some embodiments (e.g. as per the carbogenically-coated silica nanoparticles) purification takes place before pyrolysis and just after formation of the coupled carbogenic precursor(s).

The purified CNPs are suitably dried, which may involve removal of solvent(s), such as dispersion solvents used during the purification. In preferred embodiments, the drying of CNPs involves lyophilisation (freeze drying) to yield fine CNPs.

The CNPs produced by the methods of the invention suitably have any one or more properties described herein in relation to CNPs. Suitably, the one or more carbogenic precursor(s) or carbogenic precursor group(s) (e.g. of a coupled carbogenic precursor(s)) are carbonised (most suitably pyrolysed) to yield carbonaceous material. Such carbonaceous suitably has a minimum carbon content. The carbon content is suitably measurable by elemental analysis. Where the carbonaceous material is is mixed with and/or attached to non-carbogenic particles and/or non-carbonaceous material(s), the carbon content of the carbonaceous material per se may still be determined (suitably by elemental analysis), though this may involve performing suitable calculations to subtract any contribution from the non-carbogenic nanoparticles and/or non-carbonaceous material(s)—by way of example this may be achieved by performing an initial elemental analysis of the relevant non-carbogenic nanoparticles and/or non-carbonaceous material(s) without any carbogenic precursor(s) or carbogenic precursor group(s) present, and subsequent elemental analysis with the carbonaceous material(s), carbogenic precursor(s), and/or carbogenic precursor group(s) present. The method suitably involves forming carbonaceous material having a carbon content as defined above in relation to the CNPs.

The CNPs may then suitably be used to form a powder composition as defined herein.

Kit of Parts

According to a further aspect of the present invention there is provided a kit of parts comprising a fingerprint powder and carbogenic nanoparticles.

The fingerprint powder may be any fingerprint powder, including those already made available to the public. The fingerprint powder may be a fingerprint powder as defined herein in relation to the diluent of the fingerprint powder composition of the invention.

The carbogenic nanoparticles are suitably as defined herein.

According to a further aspect of the present invention, there is provided a fingerprint kit (kit of parts) comprising a fingerprint powder composition as defined herein, and one or more items selected from:

i) One or more further fingerprint powders (e.g. one or more colours thereof);
ii) One or more magnetic powders (e.g. one or more colours thereof);
iii) One or more fluorescent powders (e.g. one or more colours thereof);
iv) Fingerprint lifting tape (suitably transparent);
v) One or more fingerprint lifting cards;
vi) Cutting device (e.g. scalpel, scissors);
vii) One or more fingerprint brushes;
viii) One or more magnetic applicators;
ix) Imaging apparatus (e.g. UV lamp and/or a camera or other suitable imaging device).

Method of Fingerprinting/Visualising

The present invention provides a method of fingerprinting (or method of visualising or dusting for fingerprints), suitably as defined herein. The method suitably involves, at some stage, producing an imagable impression pattern using a powder composition as defined herein. As such, the present invention suitably provides an imagable impression pattern or a tape-lifted imagable impression pattern obtainable by, obtained by, or directly obtained by the method of fingerprinting (or method of visualising or dusting for fingerprints) as defined herein.

The method of fingerprint suitably comprises coating a surface, comprising or suspected of comprising a latent fingerprint, with a powder composition as defined herein. The method suitably involves developing an imagable impression pattern of the latent fingerprint within or from the coating of powder composition, though such "developing" may occur simultaneously with the coating step.

In some embodiments, the imagable impression pattern may be suitably extracted from a surface via a process known as "tape-lifting". As such, the method may optionally involve tape-lifting said imagable impression pattern of the latent fingerprint from the surface. However, imaging may optionally occur in situ whilst the imagable impression pattern remains upon the surface comprising or suspected of comprising a latent fingerprint.

The method suitably involves imaging (e.g. photographing) the imagable impression pattern of the latent fingerprint, whether the imagable impression pattern is a tape-lifted the imagable impression pattern or whether the imagable impression pattern remains in situ upon the surface comprising or suspected of comprising a latent fingerprint.

i) Coating Surface

Coating the surface with the fingerprint powder composition may involve applying the composition (to said surface with a fingerprint brush. Fingerprint brushes are known in the art, and have very fine fibres/bristles to enable them to retain fingerprint powders and deposit them gently upon the latent fingerprint residing on the surface without obliterating the latent fingerprint. Alternatively, the surface may be coated by simply blowing the fingerprint powder composition across the surface and/or latent fingerprint.

Where the fingerprint powder composition comprises a magnetic powder, the surface (or relevant part thereof, for instance, bearing the latent fingerprint) may be coated using a magnetic applicator which may, for instance, be moved gently over the surface or latent fingerprint.

Coating of the surface yields a developer-coated surface.

ii) Developing Imagable Impression Pattern

Developing of the imagable impression pattern may occur simultaneously with coating step (i) if a latent fingerprint becomes instantly visible or imagable or else becomes instantly more visible or imagable during or directly after said coating step. However, more typically developing of the imagable impression pattern involves removing excess fingerprint powder composition, suitably so as to leave upon the surface only fingerprint powder composition associated with (or adhered to) a latent fingerprint and/or the fingerprint residues thereof. Typically, therefore, once the fingerprint developer composition has been coated upon the surface (or relevant part thereof), any excess composition may be removed, for example, by blowing away the excess.

Following development, the fingerprint pattern should be imagable (e.g. through taking a photograph, and/or with specialist equipment, such as UV-lamps, for instance, to facilitate fluorescence)—i.e. an imagable impression pattern.

Development of the developer-coated surface yields a developed surface.

iii) Tape-lifting the Imagable Impression Pattern

Once an imagable impression pattern has been developed upon the surface, said pattern may be tape-lifted off said surface. This suitable involves carefully adhering fingerprint tape to the developed imagable impression pattern and subsequently removing said tape therefrom. This process suitably transfers the fingerprint powder composition (which forms or within which is formed an imagable impression pattern of the latent fingerprint) from the surface onto the tape.

The tape bearing the imagable impression pattern, suitably upon an adhesive side thereof, may then be imaged, stored, or further processed (e.g. forensically examined). The tape bearing the imagable impression pattern may be termed a tape-lifted imagable impression pattern.

iv) Imaging the Imagable Impression Pattern

The imagable impression pattern may be imaged either in situ upon the surface upon which the imagable impression pattern was developed or else upon tape to which the imagable impression pattern has been transferred (if a tape-lifting step was involved). Further details regarding the imaging of the imagable impression pattern are given below.

Method and Apparatus for Imaging an Imagable Impression Pattern

The present invention provides a method and apparatus for imaging (or otherwise visualising) an imagable impression pattern. Such methods and apparatuses may be utilised in a forensic laboratory (e.g. to analyse objects and evidence obtained from a crime scene, or to examine or record tape-lifted imagable impression patterns taken from a crime scene) or in situ (e.g. at a crime scene). The apparatus may be used to facilitate a search for latent fingerprints, especially against backgrounds which are notoriously difficult to image against, or may be used to produce a record of a given latent fingerprint or in the analysis thereof (including in fingerprint matching).

The apparatus suitably enables imaging of an imagable impression pattern (suitably one that is obtainable by the aforedescribed methods) upon a background surface, suitably upon any background surface regardless of the appearance (e.g. colour, pattern) and/or texture of said surface.

The apparatus suitably comprises a variable (or tunable) wavelength radiation source. The radiation source is suitably selectively tunable to emit incident or input radiation of one or more given wavelengths. The method suitably involves exposing the imagable impression pattern to said input radiation. Where appropriate input wavelength(s) are selected, such exposure suitably facilitates visualisation of the imagable impression pattern against the background surface, and suitably enhances the contrast between the imagable impression pattern and the background surface. Further details are given below.

The apparatus suitably comprises an imaging device. The imaging device is suitably operable to capture an image of the imagable impression pattern, suitably whilst said imagable impression pattern is exposed to the relevant input radiation. In this manner, it is suitably possible to capture enhanced, clear images (whether temporarily, such as in real-time with the naked eye, or in an otherwise more permanent form) of the imagable impression pattern. Further details are given below.

The apparatus suitably comprises an image storage medium for storing an image captured by the imaging device. This enables the enhanced images obtainable through using the present invention can be stored and potentially used at a later stage, for instance, in fingerprint matching or other forms of forensic analysis. Further details are given below.

In an embodiment, the apparatus is operable to capture multiple images of the imagable impression pattern, most suitably whilst the imagable impression pattern is being exposed to various different wavelengths of input radiation, suitably to thereby cause the imagable impression pattern to fluoresce in various different colours against a given background (suitably the background appears substantially the same in each image). In this manner, multiple images may be taken so that the clearest images (i.e. those exposed at an optimal input wavelength(s)) may be identified later. This may be particularly important if the input wavelength(s) for optimal imaging against a given background are unknown to a user of the apparatus at the time of imaging. However, alternative solutions to this issue involve the use of automated background-compensation software (see below).

Imagable Impression Pattern, Background Surface, and the Properties Thereof

As aforementioned, the present invention provides an imagable impression pattern or a tape-lifted imagable impression pattern. The imagable impression pattern is suitably formed by the powder composition, and is most suitably distributed in a distinctive pattern upon the background surface (or tape) that suitably corresponds with a characteristic pattern of underlying later fingerprints. The appearance of the powder composition itself within the imagable impression pattern may be a particular single colour (e.g. white), suitably depending on the colour of the diluent, though background light may well cause the CNPs present within the powder composition to fluoresce at particular output wavelengths, typically depending on the spectral properties of the background lighting. However, the fluorescent properties of the powder composition (caused by the presence of the CNPs) suitably become most apparent when background light/radiation is minimised or eliminated, and the imagable impression pattern is directly irradiated with radiation from the variable (or tunable) wavelength radiation source.

The background surface itself may be any background surface. A particular advantage of the invention is that imagable impression patterns can be viably and clearly visualised and/or imaged against a wide variety of backgrounds, suitably through judicious tuning of the input wavelength(s).

Variable (or Tunable) Wavelength Radiation Source

The variable wavelength radiation source suitably comprises a radiation emitter (or lamp), suitably a radiation emitter capable of emitting radiation (i.e. input/incident radiation) having wavelength(s) (suitably exclusively) in the range of 1000 nm to 10 nm, suitably 700 nm to 100 nm, suitably 700 nm to 300 nm. Suitably, the wavelength(s) of the emitted radiation is variable/tunable, suitably between the aforesaid wavelength values. The wavelength(s) of the emitted radiation (including the distribution thereof) may be manually and/or automatically variable/tunable. Different wavelengths and/or distributions thereof may be obtained by using appropriate filters (e.g. filters configured to selectively filter blanket radiation or radiation having a wide distribution of wavelengths to thereby only permit emission of a relatively narrow range of wavelengths). Alternatively, the emission spectrum (or distribution of wavelengths) may be determined by the emission source (e.g. a material which only emits at certain wavelengths).

In some embodiments, the variable wavelength radiation source may be configured to emit radiation of one or more wavelength(s), and possible emit blanket radiation of a variety of wavelengths. Most suitably, regardless of how the variable wavelength radiation source functions, it is suitably tunable to emit radiation of different wavelengths or radiation exhibiting a different distribution (e.g. in terms of intensity) of wavelengths. Most importantly, the variability or tunability suitably allows the appearance of imagable impression patterns and/or powder compositions of the invention to be varied against the background surface (suitably by varying the output colour).

It will be understood by the skilled person that references to "incident/input radiation at one or more (manually and/or automatically) selected wavelengths" and/or corresponding "output radiation" preferably includes a (manually and/or automatically) selected distribution of wavelengths, since varying the input wavelength distribution will generally change the output wavelength distribution as well (and hence the appearance of an imagable impression pattern). Bandwidths of input and corresponding output radiation will largely depend on the quality and/or configuration of the apparatus in question. References herein to a "distribution of wavelength(s)", suitably refers to radiation (e.g. blanket radiation) of multiple wavelengths of various relative intensities (suitably different relative intensities). For instance, blue light may be described as a distribution of wavelengths whose relative intensities cause the light to appear blue.

The method suitably involves exposing the imagable impression pattern to radiation emitted by the variable wavelength radiation source (i.e. input radiation). Suitably the input radiation is tuned, optionally after one or more prior exposures of the imagable impression pattern to input radiation (suitably at different wavelengths or distributions thereof) to allow for determination of appropriate input radiation for the given background surface (e.g. for optimal or adequate visualisation and/or imaging). However, where the user has already pre-determined the appropriate input radiation (e.g. whether through knowledge, experience, or by reference to pre-produced instructions or guidelines relating to appropriate input radiation for various background surfaces) the user may tune the variable wavelength radiation source without necessarily conducting initial exposure tests (though initial exposure tests may facilitate fine tuning). Suitably the variable wavelength radiation source is tunable, or at least fine-tunable. However, suitably the variable wavelength radiation source may be automatically tunable, for instance where the imaging apparatus is capable of automatically pre-determining appropriate input wavelength(s) (or distribution(s) thereof) on the basis of the background surface, the nature of which a computer may be able to analyse.

Most suitably, background radiation is minimised or eliminated (e.g. by turning all lights off or using a dark room) before exposing the imagable impression pattern to radiation emitted by the variable wavelength radiation source.

Imaging Device

The imaging device suitably facilitate visualisation and/or image capture of the imagable impression pattern.

The imaging device suitably comprises an optical lens, suitably to enable visualisation of an (preferably exposed) imagable impression pattern therethrough. The optical lens is suitably capable of magnifying the imagable impression pattern. The imaging device or optical lens thereof may be suitably equipped with lens filters to further facilitate visualisation and/or imaging. For instance, lens filters may be used to minimise certain features of the background surface. In a particular embodiment, the optical lens is a microscope lens and/or the imaging device comprises a microscope.

The imaging device is suitably capable of capturing images. As such, the imaging device suitably comprises a camera, suitably a camera that is capable of capturing wavelengths as defined hereinbefore.

In a particular embodiment, the imaging device comprises both a microscope and a camera.

Suitably, the imaging device is connected to or otherwise associated with the variable wavelength radiation source, suitably as part of a fully integrated imaging apparatus.

The method suitably involves capturing an image of the imagable impression pattern during its exposure to the incident radiation (preferably incident radiation of a wavelength(s) or distribution thereof which enables visualisation of the imagable impression pattern). Suitably such image capture is performed with a camera, suitably in conjunction with a suitable optical lens optionally equipped with one or more lens filters.

Image Storage Medium

Suitably, the imaging apparatus may comprise or be otherwise associated with (or able to communicate with, whether in a wired or wireless fashion) an image storage medium. Though the image storage medium may simply be photopaper or such like, most suitably the image storage medium is a digital storage medium capable of storing data, such as a computer-readable medium (e.g. hard disc, USB drive, SD card, remote or local server, etc.). Suitably, a captured image is therefore stored in the image storage device.

Multiple Imaging Cycles

The apparatus may optionally capture multiple images of the imagable impression pattern, with each imagable impression pattern suitably exhibiting a different appearance (suitably a different colour) against a given background (which suitably does not change in appearance when input wavelength(s) and/or distributions thereof are adjusted). This allows a forensic investigator to judiciously choose the best image to work with or examine at a later stage. However, multiple imaging may form part of a method involving automated background-compensation, whereby a number of images are captured (suitably of different appearance) and, on the basis of the different images, a computer may determine the most appropriate input wavelength(s) (or distribution thereof), optionally via operation of a computer algorithm or comparative database.

Computer Implementation (Automated Wavelength Selection)

The methods of imaging defined herein may be computer-implemented, whether partially or fully. A computer-implemented method (and a corresponding apparatus) still employs a variable (or tunable) wavelength radiation source, an imaging device, and an image storage medium, as defined hereinbefore, but additionally employs a background surface analyser to analyse the background surface and, on the basis of the analysis of the background surface, select one or more suitable wavelengths (or distributions thereof) for the incident radiation. As such, the imaging apparatus suitably comprises a computer to control the background surface analyser, and most suitably to control one or more of the other elements of the imaging apparatus. Suitably, one or more data transfer channels (be them wired or wireless) mediate the transfer of data, information and/or control instructions between the computer and any relevant components of the apparatus. Suitably instructions are issued by the computer to the relevant component(s) via relevant data transfer channels, whereas data and information may be transfer to and from the computer.

The aforementioned method steps relating to exposing the imagable impression pattern, capturing an image, and storing the captured image are suitably all computer controlled. However, the method step of tuning is also suitably computer controlled, and suitably involves a computer analysing the background surface, determining appropriate input wavelength(s) (or distributions thereof), and automatically tuning the variable (or tunable) wavelength radiation source.

Background Surface Analyser

The imaging apparatus suitably comprises a background surface analyser, suitably as defined herein.

The background surface analyser suitably comprises a background surface detector. The background surface detector is suitably operable (whether automatically or otherwise, most suitably automatically) to obtain background surface information. The background surface information suitably relates to the nature of the background surface (be it in terms of its appearance, texture, or nature). Suitably the background surface information may be one or more captured images of the background surface (or data relating thereto), suitably in the absence of any exposure to input radiation though optionally the captured images may include one or more images obtained whilst the background surface (optionally in the presence or absence of an imagable impression pattern or powder composition sample) was exposed to input radiation (optionally at different wavelength(s) or distributions thereof). Obtaining background surface information during different input wavelength exposures may suitably equip the computer with more background surface information to enable more appropriate tuning of the input wavelength(s) before ultimate image capture and storage. The background surface information may also comprise foreground information (e.g. information regarding the imagable impression pattern or portion of powder composition, suitably relative to the background surface), especially where such background surface information is obtained during one or more incident radiation exposures (e.g. information relating to an imagable impression pattern and/or portion of powder composition, in particular relating to the appearance thereof, especially relative to the appearance of the background, particularly information regarding visibility of the foreground against the background surface).

The background surface detector may therefore comprise an imaging device as defined herein. The background surface detector may be the same as or comprise the same imaging device as defined hereinbefore so as to prevent duplication of components. Suitably the background surface detector operates in response to computer-implemented instructions (which are suitably generated and/or conveyed to the background surface detector in response to a user input or trigger, such as pressing an imaging button or a background-compensation button to trigger background analysis). Background surface information obtained by the surface detector is suitably conveyed back to the computer and optionally stored (optionally temporarily or permanently).

The background analyser suitably comprises a computer. The computer suitably runs pursuant to background surface analysis software. Suitably such background surface analysis software configures and/or causes the computer (optionally in conjunction with other inputs, such as inputs via a user interface) to communicate with and control a background surface analyser and/or the constituent parts thereof, though suitably the background surface analysis software may be a part of or otherwise associated with comprehensive computer control software which may optionally operate and/or control other elements of the apparatus (e.g. variable wavelength radiation source, imaging device, image storage medium, and/or any other auxiliary components). The software code of the aforedescribed software suitably configures, operates, and/or causes the computer to implement any, some, or all of the operations/method steps defined herein, when the software code is executed on the computer.

The computer is suitably configured or operable to operate a background surface detector, suitably by conveying appropriate instructions and/or data to the background surface detector. The computer may cause operation of the surface background surface detector, and/or may cause the background surface detector to obtain background surface information:

i) before providing (e.g. coating and developing) an imagable impression pattern upon the background surface;

ii) after providing (e.g. coating and developing) an imagable impression pattern upon the background surface;

iii) whilst any, some, or all of the background surface, imagable impression pattern (where present), and/or a portion of powder composition (whether positioned upon the background surface or otherwise) is exposed to incident/input radiation at one or more (manually and/or automatically, preferably automatically set by the computer itself in response to pre-obtained background surface information and/or prior analysis thereof) selected wavelengths (or distribution(s) thereof) (whether these exposures and/or the obtaining of background surface information occur simultaneously, sequentially, separately, or otherwise); and/or iv) whilst any, some, or all of the background surface, imagable impression pattern (where present), and/or a portion of powder composition (whether positioned upon the background surface or otherwise) is not exposed to incident/input radiation;

and/or the background surface information may comprise information obtained in any, some, or all of the aforementioned circumstances i) to iv), optionally after multiple cycles of obtaining background surface information under the any, some, or all of the aforementioned circumstances (optionally with different exposure wavelengths and/or distributions thereof). Where the background surface information is obtained via multiple cycles, the method may suitably involve intervening computer-implemented analysis of partial background surface information to furnish pre-obtained background surface information which may then be used in further cycles of information obtaining and. or analysis. Such analysis steps may be performed as defined elsewhere herein. In this manner the computer may suitably operate and/or tune a variable wavelength radiation source, an imaging device, and/or the background surface detector accordingly during the obtaining of background surface information. Such devices may be operated as defined anywhere herein, suitably under the control of the computer.

The aforementioned pre-obtained background surface information (and/or analysis thereof), which may optionally be used in the automatic setting of the wavelength(s) and/or distribution thereof of incident/input radiation, may be obtained following one or more previous cycles of obtaining background surface information and/or analysis thereof. Such previous cycles may be performed under any of the aforementioned conditions/circumstances, suitably in order to provide a viable starting point for developing appropriate exposure wavelength(s) (and/or distributions thereof) for ultimate imaging. Alternatively or additionally the pre-obtained background surface information may be provided by a user or by a background surface reference database (with which the computer may communicate or may essentially form a part of the computer software itself). By way of example, some preliminary background surface information obtained by the computer (e.g. from an initial image taken by the imaging device) may be analysed and/or compared to reference background surface information stored in a background surface reference database (i.e. information regarding backgrounds previously screened with corresponding information regarding appropriate input wavelengths/distributions) to yield pre-obtained background surface information which can assist operation of the background surface analyser. This may assist by providing a good starting point for determining appropriate input radiation and/or fine tuning of the input radiation.

Suitably, after some or all of the background surface information has been "obtained", the background surface information is suitably conveyed to the computer suitably from the background surface detector.

Upon or after receipt of the background surface information, the computer is suitably configured or operable to analyse the background surface information.

Analysis of background surface information may involve comparative analysis with pre-obtained background surface information, such as that obtained from a database as described above (which includes where the software itself contains the relevant data of the database), and subsequent determination of preferred output radiation (be it approximate and in need of further fine tuning, or be it a final determination) for optimal visualisation/imaging of a fingerprint impression pattern against the given background surface. For instance, analysis may involve determining the "prevailing background colour" (i.e. the dominant colour or an arbitrary colour ascribed to the background for the purposes of conducting approximate analysis—this may be applied even where the background is patterned) of the background surface and thereafter determining an appropriate foreground colour (e.g. for optimal visualisation/imaging or contrast with the background). For example, where the computer detects a red background surface, the analysis may determine yellow or white to be the most appropriate foreground colours. Such a determination may be a final determination, or may merely serve as a preliminary determination or a starting point from which fine tuning of the input radiation may ensue.

Alternatively or additionally (especially where only a preliminary determination is provided for an appropriate foreground) analysis of background surface information may involve analysis of background surface information obtained (optionally via multiple cycles) whilst any, some, or all of the background surface, imagable impression pattern (where present), and/or a portion of powder is exposed to incident/input radiation. Such a method may provide more flexibility in that the apparatus may better respond to the properties of a particular powder composition in use (which may vary in composition and consequent vary in terms of their excitation-dependent emission properties). Such analysis may involve deploying appropriate computer algorithms (such as those well known in the art, for instance in graphic design software, such as Adobe Photoshop®) which determine, on the basis of the background surface information (which may include information on both background and foreground at certain incident exposure wavelengths/distributions) which is the most appropriate foreground for optimal visualisation/imaging (e.g. best contrast and/or best colour combination). This analysis may require multiple cycles of exposure at different wavelength/distributions until optimal input radiation has been determined. In this manner, the variable wavelength radiation source may tuned during the background surface analysis process or, where the background surface information and computer analysis permits, the variable wavelength radiation source may be tuned once enough background surface information has been analysed in order to make a sufficiently accurate determination of optimal input radiation.

The background analyser may therefore be configured and/or operable to fine tune the variable wavelength radiation source and/or input radiation by one or more further cycles of background surface information analysis/tuning steps.

Whether tuning occurs during the background analysis process or after, suitably the computer automatically tunes variable wavelength radiation source and automatically selects a preferred one or more wavelength(s) (or distribution) of the incident radiation.

The computer may, at any stage, whether during background analysis and/or imaging, initiate exposure, imaging (including image capture), and/or image storage, optionally though one or more repeat cycles optionally with different input wavelength(s) (or distribution(s)) and/or with different imaging parameters (e.g. camera settings, e.g. exposure settings depending on darkness, contrast, lens filters, etc. . . . ).

The computer may be configured and/or operable to send captured images or data relating thereto to various authorised parties.

The computer may be configured and/or operable to transfer captured images to a central image database (or place captured images to a queue for future inclusion therein).

An imaged impression pattern may be printed, scanned (e.g. into a computer), uploaded (e.g. to a computer or storage medium), and/or otherwise stored for future reference or comparison. In a particular embodiment the imaged impression pattern may be uploaded or scanned into an Automated Fingerprint Identification System (AFIS).

The computer may be configured and/or operable to send or add obtained background surface information (and/or analytical results relating thereto—e.g. optimal foregrounds, optional imaging parameters relating to the imaging device) to a central background surface reference database (or place captured images to a queue for future inclusion therein). Where a particular background surface is new, information and exposure/imaging settings may be conveyed to a central background surface reference database to facilitate future imaging. Alternatively image of (or data relating to) the background surface may be conveyed elsewhere for further study. Such information and settings may include images of the relevant blank background, before and after applying fingerprint powder, with or without exposure with input radiation. The properties of the relevant background may also be later analysed and/or correlated with known backgrounds stored in a pre-established background database to facilitate criminal investigations (e.g. where the background surface of an article abandoned at a crime scene is known, the relevant database may be able to facilitate identification of the background, from where the relevant article was obtained or purchased, and this may provide leads that facilitate capture of a culprit or owner of the relevant fingerprints).

The computer may be configured and/or operable to use captured images in fingerprint matching, which may optionally be performed in situ by the same computer and/or by a different computer or user with appropriate authentication/permissions.

Computer Software

The present invention provides a computer program, suitably as defined herein. Suitably the computer program comprises software code for performing the computer-implemented method of imaging an imagable impression pattern defined herein when the computer program is run on a computer.

The computer program may comprise background surface analysis software (or code relating thereto). Background surface analysis software (or code relating thereto) suitably configures a computer to perform background analysis, suitably as defined herein (e.g. which suitably involves operating and/or controlling a background surface analyser).

Alternatively and/or additionally, the computer program may comprise computer control software (or code relating thereto). Computer control software (or code relating thereto) suitably configures a computer to operate and/or control other components of the apparatus, such as a variable (or tunable) wavelength radiation source, an imaging device, and/or an image storage medium. Suitably the computer control software (or code relating thereto) is integrated with or otherwise associated with background surface analysis software (or code relating thereto) such that the computer program may control the entire apparatus automatically, optionally after a manual trigger (e.g. user input such as pressing a trigger button when the exposure and/or imaging device is positioned to expose and/or image).

The computer program may comprise one or more pieces of computer software or sets of software code performing different functions. Some software code may operate a background analyser, other software may perform analysis, other software may operate other component parts of the apparatus. Suitably an overarching computer program integrates all the relevant software to co-ordinate the functioning thereof.

The present invention also provides a computer-readable medium comprising software code executable to cause a computer to perform the computer-implemented method of imaging an imagable impression pattern defined herein when the software code is executed on a computer.

Wherever a computer is described as being configured to and/or operable to cause a particular operation or method to be implemented, said computer is suitably configured to and/or operable to do so by virtue of software code pursuant to which the computer runs.

Fingerprint Matching/Use of Imaged Impression Pattern

According to a further aspect of the present invention, there is provided a use of an imaged impression pattern as defined herein in fingerprint matching (or to obtain a fingerprint match), for example, by comparing the imaged impression pattern to one or more comparative fingerprint images (or else comparing data relating to the imaged impression pattern with data relating to one or more comparative fingerprint images).

According to a further aspect of the present invention, there is provided a method of fingerprint matching (or identifying a fingerprint), the method comprising comparing an imaged impression pattern as defined herein with one or more comparative fingerprint images (or else comparing data relating to the imaged impression pattern with data relating to one or more comparative fingerprint images).

An imaged impression pattern, representative of latent fingerprints upon a surface (e.g. at a crime scene), can be correlated with the fingerprint(s) of a specific individual (and the fingerprints thereby identified) by simply comparing said imaged impression pattern with one or more comparative fingerprint images (or else comparing data relating to the imaged impression pattern with data relating to one or more comparative fingerprint images). Such a comparison may be performed manually or automatically (e.g. using a computer and/or algorithms).

In a particular embodiment, the fingerprints represented by the imaged impression pattern are identified using an automated fingerprint identification system. This involves automatically matching one or more unidentified fingerprints against a database of known (and potentially unknown) fingerprints. Typically, the imaged impression pattern is first transferred (e.g. by uploading or scanning) to a computer (or other relevant automated machinery). The computer, which is suitably programmed with and running pursuant to specialist fingerprint identification software and is linked to a database of known (and potentially unknown) fingerprints, may then compare said imaged impression pattern (or data obtained therefrom—e.g. data points relating to characteristic features of minutiae) with any or all fingerprints held within the database. Suitably, if a "match" is found (i.e. if the comparison with comparator fingerprints identifies sufficient similarities to meet the pre-determined criteria of a fingerprint match), the computer reports that a match has been found and optionally reports the comparative fingerprints with which the imaged impression pattern matches. If no match is found, the database may be amended to create an additional database record including the imaged impression pattern (or data relating thereto, e.g. data used in fingerprint matching algorithms) and any relevant associated information (e.g. time, data, place, surface, circumstances, case number, in relation to which the latent fingerprints represented by the imaged impression pattern were developed/imaged).

Various fingerprint matching algorithms may be employed. Suitably such algorithms are optimised to minimise false positive and false negative error rates. Such algorithms may be attuned to accommodate image rotation variance and may function by reference to a core reference point (e.g. at the center of the relevant fingerprint pattern). Such algorithms may be extremely robust, and be capable of fingerprint matching even the poorest quality imaged impression patterns. However, an advantage of the present invention is the high quality of the imaged impression patterns obtained. As such, the present invention permits the use of less robust algorithms (thereby reducing the computation burden) and/or yields fewer false positive/negatives. Minutiae confidence rates and match probability scores (such as those generated by commonly used AFIS systems) are likely to be much greater when using fingerprint powder compositions of the invention.

The database in question may be a local, national, regional, or international fingerprint database (e.g. AFIS).

The fingerprint powder compositions of the invention may be additionally used to provide imaged impression patterns of fingerprints of known identify. In this manner, a more accurate fingerprint database may be established, which suitably allows for more accurate fingerprint matching. Such a database may be for criminal purposes or even civil purposes (e.g. as with an automated fingerprint verification system). An automated fingerprint verification system comprising or connectable to a database including imaged impression patterns of the invention (and/or data relating thereto) may facilitate verification of an individual's identity in order to implement attendance or access controls (e.g. as a means of fingerprint authentication). Alternatively, such systems and their associated databases may facilitate background checks on individuals, such as CRB checks (as presently used before appointing individuals to sensitive roles in education, etc.).

As such, according to a further aspect of the present invention, there is provided a database comprising two or more imaged impression patterns (and/or data relating thereto) of latent fingerprints as defined herein.

EXAMPLES

Materials and Equipment

Silica dispersion (Ludox HS 30) was obtained from Sigma Aldrich.

Citric acid monohydrate, $C_6H_8O_7$ (CA) and ethanolamine, $C_2H_7ON$ (EA), were both obtained purchased from Sigma Aldrich.

$TiO_2$ (21 nm particle size) was obtained from Sigma Aldrich.

Clay Laponite was obtained from Southern Clay Products.

Clay MMT was obtained from Southern Clay Products.

Fingerprint powder-white was obtained from K9 Scene of Crime Equipment Limited.

Dialysis is performed with deionized water using a Snake Skin Pleated Dialysis Tubing membrane (with a molecular weight cutoff of 3500 Da).

Dispersions were freeze dried using Sciquip (Christ).
Elemental Analysis was performed using a Perkin Elmer 2400 II Elemental Analyser.

Thermogravimetric analysis (TGA) was performed using a TGA Q 5000 with a heating rate of 10° C./min, scanning a temperature range from room temperature up to 600° C. under flowing N2.

Transmission Electron Microscopy (TEM) images were obtained by A FEI T12 Spirit operated at 120 kV. A droplet of a sample (0.05 mg/mL in water) was deposited on a carbon coated cupper grid (Agar Scientific, USA) and dried under air.

Fluorescence microscopy images were obtained via a Zeiss Axio Scope A1 microscope through band-pass filters of different wavelengths; UV excitation, blue excitation and green excitation (dapi, gfp, texas red)

In general (though specific procedures are detailed below), to obtain the powders 1 ml of a 1 mg/mL aqueous solution of C-dots was added to a centrifuge tube, and either 100 mg or 150 mg of the different diluents. The centrifuge tubes were topped up to 35 ml of distilled water and the dispersions were immerged to liquid nitrogen. The frozen samples were then attached to a freeze-drier SciQuip Christ system and were left for 3-4 days for complete removal of the water.

Example 1—Synthesis and Characterization of "aC-dots" from Ethanolamine and Citric Acid "aC-dots", a particular form of carbogenic nanoparticles suitable for use with the present invention, were produced using a modification of a literature procedure (Krysmann et al, "Formation Mechanism of Carbogenic Nanoparticles with Dual Photoluminescence Emission", J. Am. Chem. Soc. 2012, 134, 747-750). In this example:

16.8 g of citric acid monohydrate, $C_6H_8O_7$ (CA), and 15 g of ethanolamine, $C_2H_7ON$ (EA), (both purchased from Aldrich) were mixed (molar ratio 1 to 3) and treated at 180° C. for 30 min under reflux. The heating temperature was then increased to 230° C. and the reaction was carried on for additional 30 min without the reflux condenser. The product was cooled at room temperature for several hours and it was then dispersed in water. The dispersion was then introduced on a SnakeSkin Pleated Dialysis Tubing membrane (with a molecular weight cutoff of 3500 Da) and was extensively dialyzed against deionized water (for several days), in order to remove impurities and byproducts. The purified dispersion was freeze-dried. Quantum yield was estimated 15% relative to anthracene (0.32 mg/ml in ethanol) with $\lambda_{ex}$=365 $nm^{-1}$.

Elemental analysis indicated that aC-dots are composed by 44.85% C, 5.75% H, 10.85% N.

The diameter of aC-dots falls within 15-25 nm.

FIG. 1 shows a TEM image of aC-dots having a particle size between 15-25 nm.

Example 2—Synthesis and Characterization of bC-dots from Grass

"bC-dots", a particular form of carbogenic nanoparticles suitable for use with the present invention, were produced using a modification of a literature procedure (Krysmann et al, "Photoluminescent Carbogenic Nanoparticles directly derived from crude biomass", Green Chem. 2012, 14, 3141-3145). In this example:

100 g of fresh grass were mixed with 1 l of water and then thoroughly shredded in a blender. The mixture was split into four porcelain crucibles and heated in an oven at 300° C. for 4 h in air. The approximately 10 g of carbonaceous material obtained was dispersed in water, and refluxed in a 3 M $HNO_3$ aqueous solution for 48 h. The material received was centrifuged (6000 rpm for 10 min) three times to remove large particles, then extensively dialyzed against deionized water using a Snake Skin Pleated Dialysis Tubing membrane (with a molecular weight cutoff of 3500 Da). The purified dispersion was freeze-dried.

Elemental analysis suggested that bC-dots are composed by 48.57% C, 2.64% H, 6.98% N. The diameter of aC-dots falls within 25-30 nm.

Figure 2:
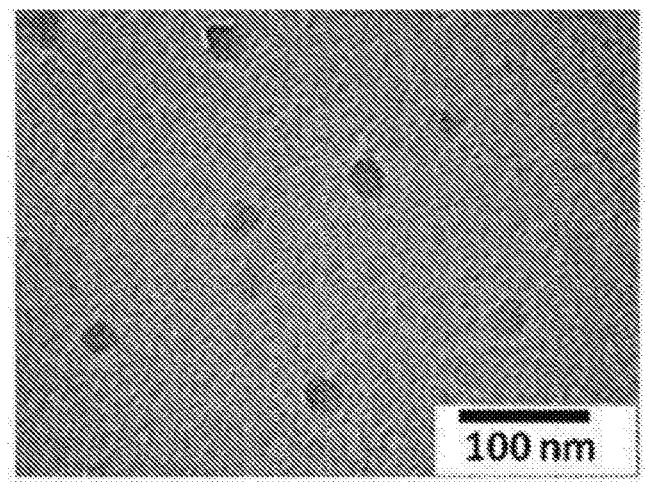
FIG. 2 shows a TEM image of bC-dots having a particle size between 25-30 nm.

FIG. 2 shows a TEM image of bC-dots having a particle size between 25-30 nm.

Example 3—Synthesis of Carbonized Silica c-$SiO_2$ 6 gr aqueous silica dispersion (Ludox HS 30 from Aldrich) was diluted with 80 g of distilled water and was placed under stirring at 70° C. 3 g of (3-Aminopropyl) triethoxysilane was added dropwise and the mixture was allowed to react for 24 h at 70° C. under reflux. The product was extensively dialyzed against deionized water using a Snake Skin Pleated Dialysis Tubing membrane (with a molecular weight cutoff of 3500 Da). The purified dispersion was freeze-dried. TGA analysis suggested that the organic content of the particles was 7 wt %. The powder was then thermally treated at 300° C. for 1 h to allow the carbonization of the organic groups.

Transmission Electron Microscopy (TEM) images were obtained by A FEI T12 Spirit operated at 120 kV. A droplet of a sample (0.05 mg/mL in water) was deposited on a carbon coated cupper grid (Agar Scientific, USA) and dried under air.

Figure 3:
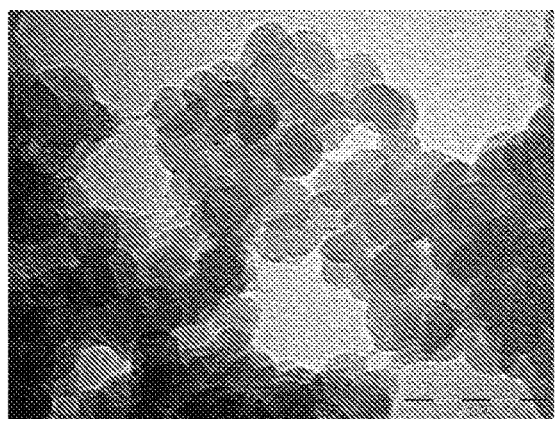
FIG. 3 shows a TEM image of c-$SiO_2$ having a particle size between about 18-20 nm.

FIG. 3 shows a TEM image of c-$SiO_2$ having a particle size between 18-20 nm.

Example 4—Preparation of Model Fingerprint Powder Compositions

Aqueous dispersions containing 1 mg of aC-dots or bC-dots (of Example 1 or 2 respectively) and 150 mg of powder A, where powder A is selected from one of those shown in Table 1:

TABLE 1 list of powders (or diluents) used in conjunction with C-dots in the production of Fingerprint Powder Compositions

| Powder number | Powder type |
| --- | --- |
| Powder A1 | $TiO_2$ (21 nm particle size) |
| Powder A2 | $SiO_2$ (Ludox HS 30) |
| Powder A3 | Clay Laponite |
| Powder A4 | Clay MMT |
| Powder A5 | FP-white |

The mixtures were freeze dried to produce the fine fingerprint powder compositions listed in Table 2.

TABLE 2

Fingerprint Powder Compositions (FPCs)

| FPC No. | CNP | Diluent | Diluent Name |
| --- | --- | --- | --- |
| A1a | aC-dots | A1 | $TiO_2$ (21 nm particle size) |
| A2a | aC-dots | A2 | $SiO_2$ (Ludox HS 30) |
| A3a | aC-dots | A3 | Clay Laponite |
| A4a | aC-dots | A4 | Clay MMT |
| A5a | aC-dots | A5 | FP-white |
| A1b | bC-dots | A1 | $TiO_2$ (21 nm particle size) |
| A2b | bC-dots | A2 | $SiO_2$ (Ludox HS 30) |
| A3b | bC-dots | A3 | Clay Laponite |
| A4b | bC-dots | A4 | Clay MMT |
| A5b | bC-dots | A5 | FP-white |

It was also discovered in separate experiments that physical solid state mixing/blending C-dots and Powder A was also highly effective, so though freeze drying may sometimes be preferred to optimise the physical form and homogeneity of a fingerprint powder composition, it is not always necessary.

Example 4.1—Alternative Preparation of Fingerprint Powder Compositions Via the Synthesis of Carbonized Material In Situ within Diluent/Precursor (uC-dots)

A preparation of C-dots from citric acid and urea (uC-dots) is now described, which employs a method whereby carbogenic nanoparticles are prepared in situ within a corresponding diluent in a single-step. The method involves using a significant excess of a diluents which itself partakes in pyrolysis and carbonization. In this example, the diluent material is urea and ultimately, after pyrolysis, pyrolysis by-products of urea.

A solid mixture of citric acid and urea in a respective weight ratio of 1:25 (though similar results were obtained using respective weight ratios of 1:50 and 1:100 as well), was first heated at 160° C. for 1 h (to fully disperse citric acid in urea) before then being exposed to one hour of pyrolysis at 230° C. The product was dispersed in water before being filtered: firstly through a Buchner filter and then through a 200 nm filter membrane. Finally, the product was freeze-dried to yield highly fluorescent powders that served as fingerprint powders in subsequent studies (see Example 6).

Example 5—Fingerprint Dusting (Generation of Fingerprint Impression Pattern)

A squirrel-hair brush was used to apply the powders to fingerprints deposited on a glass slide or on a metal surface. This produced imagable fingerprint impression patterns.

Example 6—Imaging Fingerprint Impression Pattern

The imagable fingerprint impression patterns obtained in Example 5 were then imaged using fluorescence microscopy to generate relevant images. The fluorescence microscopy images were obtained via a Zeiss Axio Scope A1 microscope through band-pass filters of different wavelengths; UV excitation, blue excitation and green excitation (dapi, gfp, texas red).

Fingerprint Powder Compositions Incorporating aC-Dots

Figure 4:
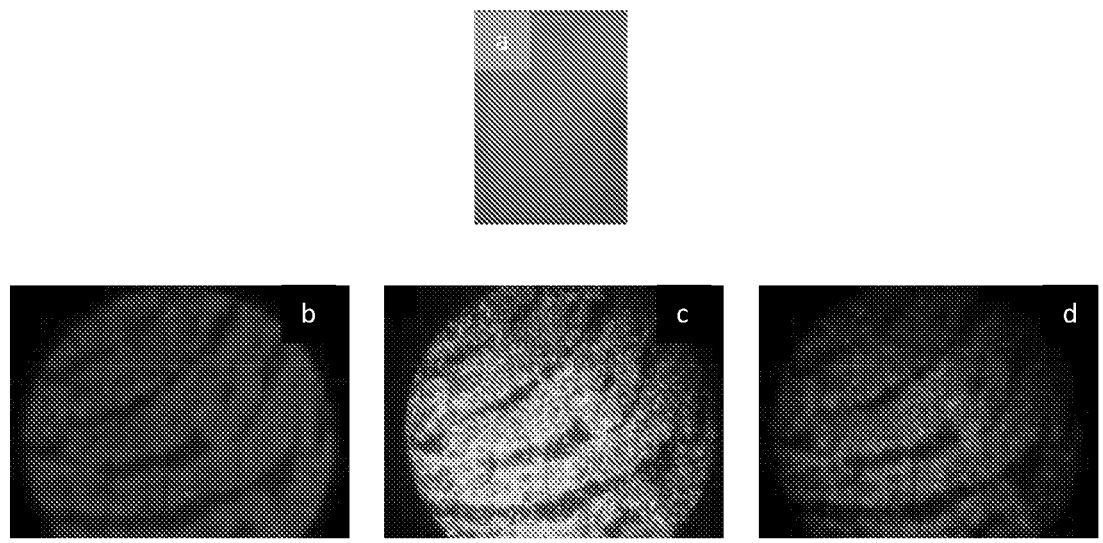
FIG. 4 shows fluescence microscopy images of (I) a fingerprint deposited on a glass slide developed with 0.7 wt % CNP-containing fingerprint powder composition A3a (aC-dots/Clay Laponite); and (II-IV) fluorescence images under different wavelength.

FIG. 4 shows fluescence microscopy images of (I) a fingerprint deposited on a glass slide developed with 0.7 wt % CNP-containing fingerprint powder composition A3a (aC-dots/Clay Laponite); and (II-IV) fluorescence images under different wavelength.

Figure 5:
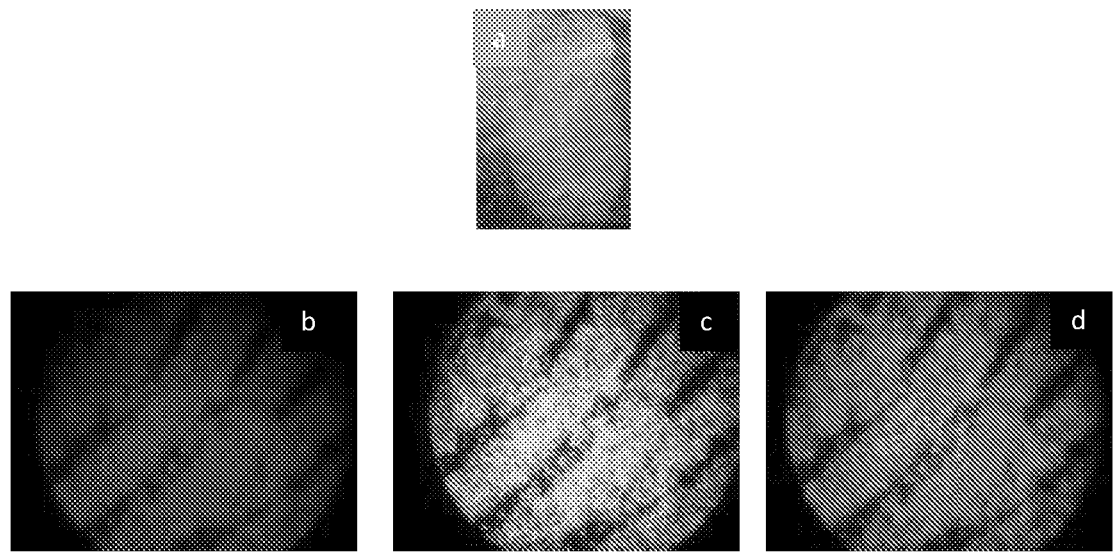
FIG. 5 shows fluescence microscopy images of (I) a fingerprint deposited on a metal surface slide developed with 0.7 wt % CNP-containing fingerprint powder composition A3a (aC-dots/Clay Laponite) and (II-IV) fluorescence images under different wavelength.

FIG. 5 shows fluescence microscopy images of (I) a fingerprint deposited on a metal surface slide developed with 0.7 wt % CNP-containing fingerprint powder composition A3a (aC-dots/Clay Laponite) and (II-IV) fluorescence images under different wavelength.

These images clearly demonstrate the universal applicability and advantages of the fingerprint powder compositions of the invention. Irrespective of the background surface upon which the imagable fingerprint impression pattern lies (e.g. metal vs glass, which are radically different in a variety of physical, chemical, and optical respects), high resolution/quality images are tunable to a variety of radically different colours. This exceptional and facile colour-tunability affords a forensic investigator instantaneous flexibility to optimise on-site viewing and image capture of latent fingerprints as well as off-site viewing (which may involve imaging of tape-lifted fingerprints). Furthermore, the flexibility to expose latent fingerprints in a variety of different colours in real time potentially assists the forensic investigator in the discovery of fingerprints which may have otherwise proved elusive. Clearly an imaging colour may be judiciously selected to optimise contrast between the imagable fingerprint impression pattern and the respective background, which is crucial given that latent fingerprints are typically found on a variety of backgrounds of numerous different colours, patterns, and textures. As such, the provision of a single fingerprint powder composition facilitating fingerprint visualisation on any background surface represents a significant contribution to the art.

The skilled person will also now readily appreciate that the fingerprint powder compositions of the invention enable automated background-compensation imaging of latent fingerprints whereby automatic determination of an optimal fingerprint imaging colour, on the basis of a background colour/pattern, triggers the automatic selection of the most appropriate exposure wavelength(s) of the variable (tunable) radiation source before imaging takes place (though optionally the automatic determination of optimal imaging colours may indeed involve pre-imaging at various wavelength(s) to deduce which wavelength(s) produce optimal images). This may involve a computer, running on appropriate computer software, determining the optimal fingerprint imaging colour (and by extrapolation the optimal exposure wavelength(s)) for a given background (which of course can be imaged and analysed by the computer, with or without a superimposed image of the selectively exposed imagable fingerprint impression pattern). For instance, where a computer detects that a background surface is substantially blue in colour, it may reasonably deduce that the fingerprints should ideally appear yellow or green in colour the final image, since these two colours tend to offer the best contrast and visualisability on a blue background. However, the selection of colour will very much depend on the algorithms (or colour determination techniques) used, which may vary depending on the requirements of the user. However, by way of example, the following background-foreground colour relationships have been identified for optimal legitability of text on a computer screen, and this may serve as guide for the determination of the best imaging colour for a given background.

A reasonable apparatus may include a tunable radiation source (e.g. which selects wavelength(s) by either selective wavelength emission or selective optical filtering of blanket radiation), an imaging device (e.g. a microscope/camera), and a computer running pursuant of specialist software which operates both the tunable radiation source and the imaging device, suitably in response to user instructions via a user interface. For example, a forensic investigator may generate an imagable fingerprint impression pattern as described above on any background surface, focus the imaging device upon the fingerprint impression pattern (e.g. with the assistance of a viewing screen), and press a single button (as a photographer would when taking a photograph). This may then initiate automated computer-implemented analysis of the background surface (optionally facilitated by comparing temporary images taken following temporary exposure, one or more times, of the fingerprint impression pattern to one or more wavelength(s)—this may be a pulsed sweep of wavelengths) followed by selection of appropriate exposure wavelength(s) before the fingerprint impression pattern is finally imaged through exposing the fingerprint impression pattern at optimal wavelength(s) determined by the computer.

Unveiling Fingerprint Facets on Multi-coloured Backgrounds by Varying Incident Wavelength—aCdots (0.7 wt %)/Silica Fingerprint Powders Using the aforementioned aC-dots (0.7 wt %)-based silica fingerprint powder systems, the photographs of FIG. 5.1 illustrate the power of the invention to resolve fingerprint patterns even on very challenging multi-coloured backgrounds.

FIG. 5.1 shows various photographs of an aC-dots (0.7 wt %)/silica-dusted fingerprint, including: a) a fingerprint deposited upon a soft drink bottle foil; b) the same fingerprint exposed under bright field illumination (poor contrast); (c) the same fingerprint exposed under fluorescence microscopy violet radiation (good contrast and facet resolution); d) the same fingerprint exposed under (e) the same fingerprint exposure under green light (only weak ridge patterns are visible); blue radiation (good contrast and facet resolution); and (e) the same fingerprint exposed under (e) the same

|  |  | Background | | | | | | | | |
|---|---|---|---|---|---|---|---|---|---|---|
|  |  | Red | Orange | Yellow | Green | Blue | Violet | Black | White | Gray |
| Foreground | Red |  | Poor | Good | Poor | Poor | Poor | Good | Good | Poor |
|  | Orange | Poor |  | Good | Poor | Poor | Poor | Good | Poor | Poor |
|  | Yellow | Good | Good |  | Poor | Good | Poor | Good | Poor | Good |
|  | Green | Poor | Poor | Poor |  | Good | Poor | Good | Poor | Good |
|  | Blue | Poor | Poor | Good | Good |  | Poor | Poor | Good | Poor |
|  | Violet | Poor | Poor | Good | Poor | Poor |  | Good | Good | Poor |
|  | Black | Poor | Good | Good | Good | Poor | Good |  | Good | Poor |
|  | White | Good | Good | Poor | Poor | Good | Good | Good |  | Good |
|  | Gray | Poor | Poor | Good | Good | Poor | Poor | Poor | Good |  |

Translating the optimal imaging colour into the relevant exposure wavelength(s) will depend on the nature of the fingerprint powder composition utilised (since factors such as CNP concentration, CNP particle size, CNP type, etc., may effect the relationship between input and output wavelengths). However, this can be easily calibrated by techniques well known in the art, and may be performed in an automated manner with the involvement of a computer which may monitor the output colour of the fingerprint impression pattern whilst a variable radiation source performs a computer-controlled sweep of some or all exposure wavelengths.

fingerprint exposure under green light (only weak ridge patterns are visible); green light (only weak ridge patterns are visible).

Fingerprint Powder Compositions Incorporating bC-dots

Figure 6:
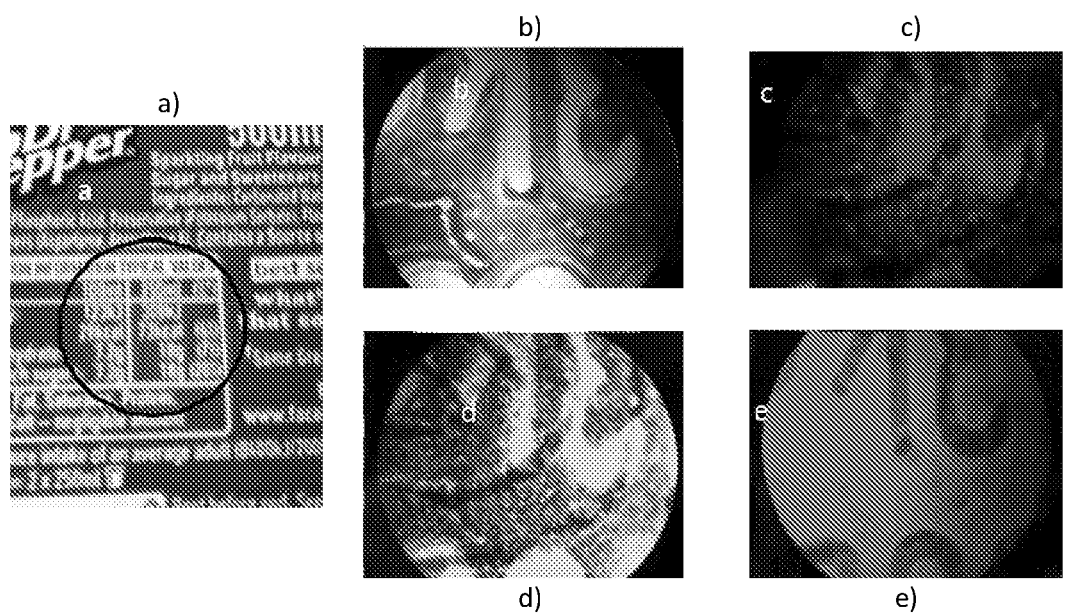
FIG. 6 shows fluescence microscopy images of (I) a fingerprint deposited on a glass slide developed with 0.7 wt % CNP-containing fingerprint powder composition A1b (bC-dots/$TiO_2$) and (II-IV) fluorescence images under different wavelength.
Figure 6:
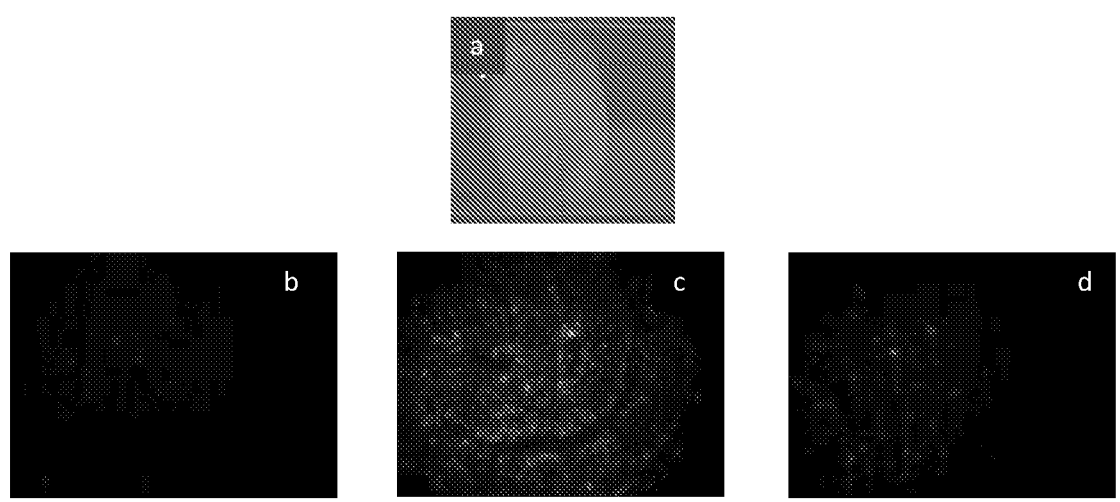

FIG. 6 shows fluescence microscopy images of (I) a fingerprint deposited on a glass slide developed with 0.7 wt % CNP-containing fingerprint powder composition A1b (bC-dots/$TiO_2$) and (II-IV) fluorescence images under different wavelength.

Figure 7:
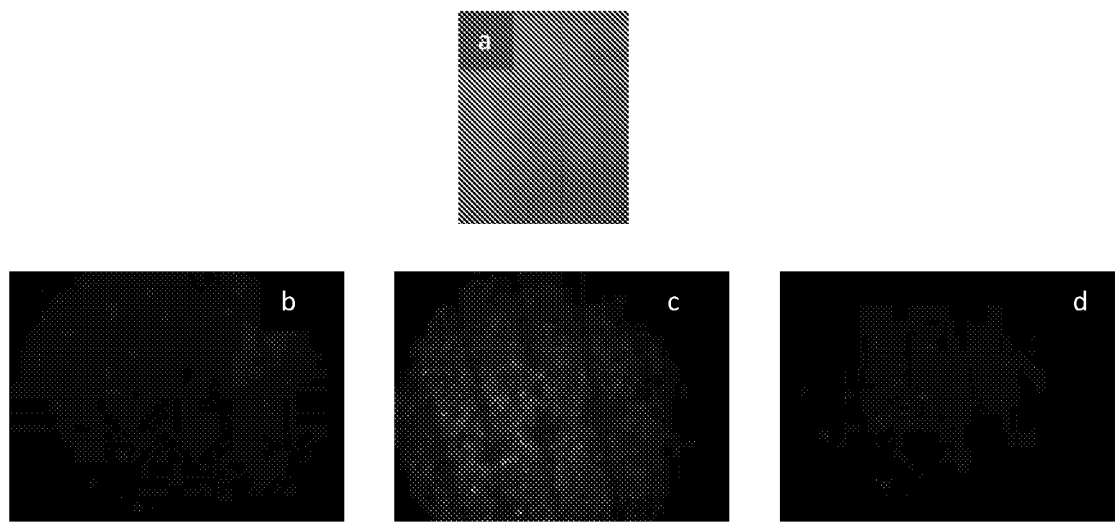
FIG. 7 shows fluescence microscopy images of (I) Fingerprint deposited on a glass slide developed with 0.7 wt % CNP-containing fingerprint powder composition A3b (bC-dots/Clay Laponite) and (II-IV) fluorescence images under different wavelength.

FIG. 7 shows fluescence microscopy images of (I) Fingerprint deposited on a glass slide developed with 0.7 wt %

CNP-containing fingerprint powder composition A3b (bC-dots/Clay Laponite) and (II-IV) fluorescence images under different wavelength.

These images illustrate that fingerprint powder compositions of the invention function with CNPs (C-dots) formed in a variety of different manners.

Fingerprint Powder Compositions Incorporating c-SiO$_2$

Figure 8:
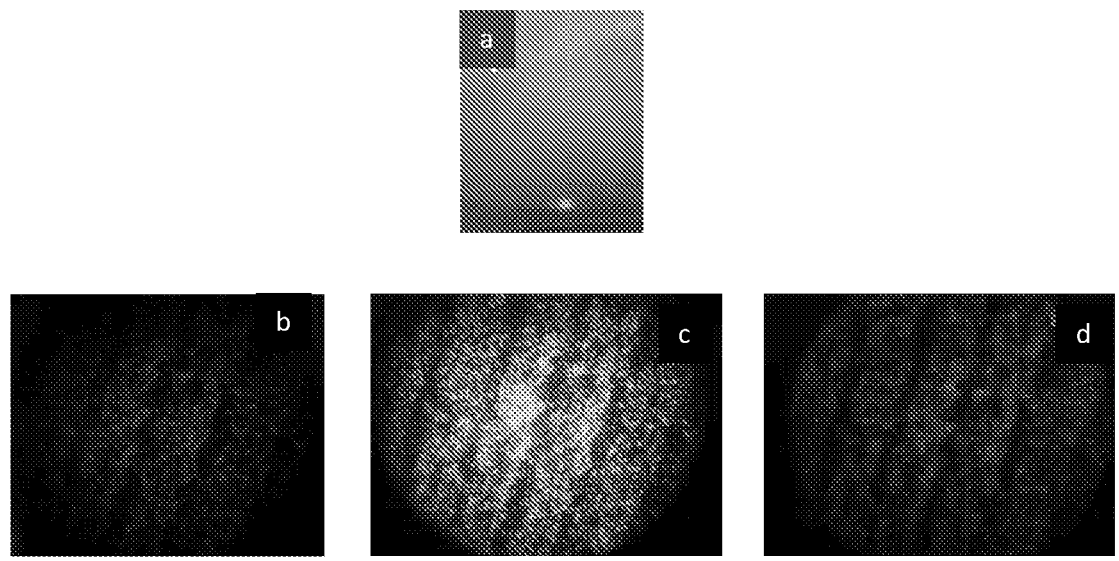
FIG. 8 shows fluescence microscopy images of (I) Fingerprint deposited on a glass slide developed with c-SiO$_2$ and (II-IV) fluorescence images under different wavelengths.

FIG. 8 shows fluescence microscopy images of (I) Fingerprint deposited on a glass slide developed with c-SiO$_2$ and (II-IV) fluorescence images under different wavelengths.

These images demonstrate that the fingerprint powder compositions of the invention justifiably extend to any nanoparticles with an exposed carbogenic surface—in this case silica nanoparticles are coated with a carbogenic or carbonised coating.

Fingerprint Powder Compositions Based on Existing Commercial Fingerprint Powders FIG. 9 shows fluescence microscopy images of (I) Fingerprint deposited on a glass slide developed with 0.7 wt % aC-dots with fingerprint powder composition A5a (Instant White Fingerprint Powder (commercial powder)) (II-IV) fluorescence images under different wavelengths.

This clearly demonstrates the broad applicability of the invention, and that existing fingerprint powder products can be very simply enhanced in terms of functionality by supplementing them with CNPs. Such retrofitting is ideal since it allows the forensic investigator to continue to use their preferred commercial fingerprint powders (or one best tailored for the particular circumstances) whilst reaping the benefits of the present invention by the simple blending of CNPs without any determinant to the original performance parameters of the commercial fingerprint powder.

Fingerprint Powder Compositions Based on the uC-dots Compositions of Example 4.1

As elucidated in Example 4.1, fingerprint powders such as the uC-dots composition described therein can be prepared in a single step, especially where the diluents is itself susceptible to carbonisation and pyrolysis as per urea in the presence of citric acid.

FIG. 9.1 shows a visualised fingerprint on a glass slide developed with uC-dots: (a) under UV light; and (b) with a fluorescent microscope (100× mag.) under violet, blue and green excitation wavelength, respectively (c, d and e).

FIG. 9.2 shows a comparison between fingerprints visualised at various wavelengths using either: a) the uC-dots powder (top row); and b) commercial fluorescent powders (bottom row). The uC-dots powder is superior, especially at certain wavelengths—here the contrast of the uC-dots developed fingerprints is superior at 475, 520, 590 nm, which is especially important where multicoloured backgrounds dictate that these wavelengths produce the optimal images.

Example 7—Use of Automated Fingerprint Identification System (AFIS)

Figure 10:
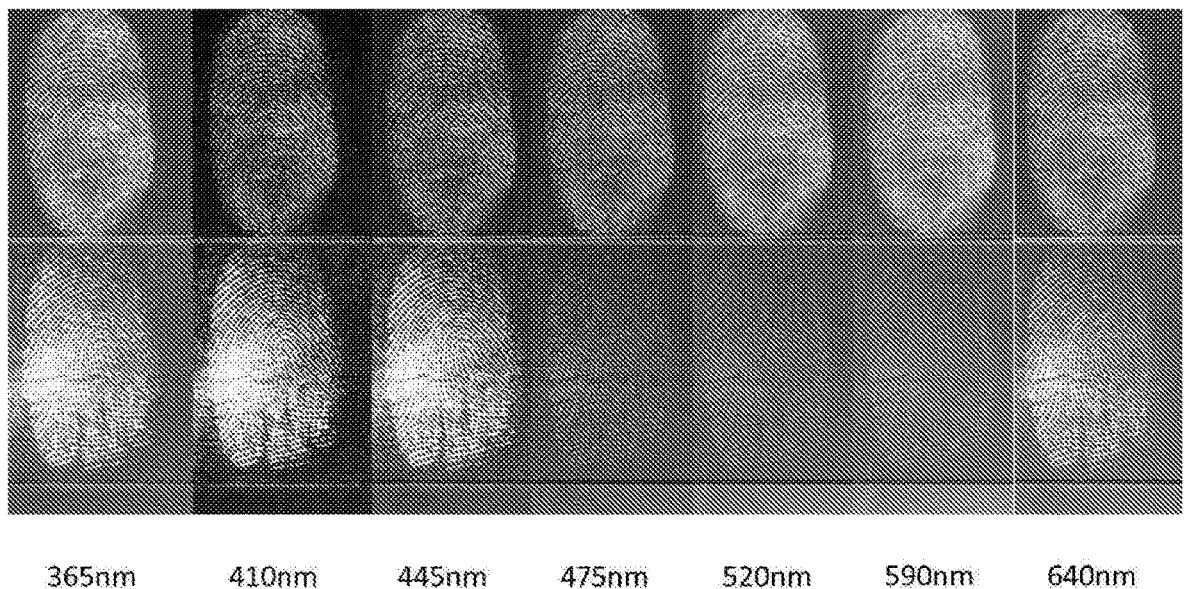
FIG. 10 shows AFIS characterisation of latent fingerprint deposited on a glass slide developed with 0.7 wt % aC-dots mixed with white fingerprint commercial powder, showing a number of minutiae detected of 31. This illustrates the high quality imageability of the fingerprint powder compositions of the invention and that such compositions are highly suited to the role of fingerprinting.
Figure 10:

FIG. 10 shows AFIS characterisation of latent fingerprint deposited on a glass slide developed with 0.7 wt % aC-dots mixed with white fingerprint commercial powder, showing a number of minutiae detected of 31. This illustrates the high quality imageability of the fingerprint powder compositions of the invention and that such compositions are highly suited to the role of fingerprinting.

The invention claimed is:

1. A method of fingerprinting, the method comprising:
   i) coating a surface, comprising or suspected of comprising a latent fingerprint, with a fingerprint powder composition;
   ii) developing an imagable impression pattern of the latent fingerprint within or from the coating of fingerprint powder composition;
wherein the fingerprint powder composition, which is for the visualization of latent fingerprints, exhibits excitation-dependent emission and comprises:
   at most 20 wt % carbogenic nanoparticles (CNPs) comprising carbonaceous material formed by carbonization of one or more carbogenic precursors, wherein the one or more carbogenic precursors are organic compounds comprising carbon, hydrogen, and oxygen; and
   a diluent;
wherein the carbonaceous material has, by elemental analysis, a carbon content of less than or equal to 60% C.

2. The method as claimed in claim 1, wherein the fingerprint powder composition comprises at least 0.1 wt % carbogenic nanoparticles and at most 10 wt % carbogenic nanoparticles.

3. The method as claimed in claim 1, wherein a carbogenic core of the carbogenic nanoparticles is responsible for at least 50% of the quantum yield within a 1000 nm to 10 nm wavelength range.

4. The method as claimed in claim 1, wherein a carbogenic nanoparticles have a particle size between 1 and 50 nm.

5. The method as claimed in claim 1, wherein the carbogenic nanoparticles are insoluble in water and hexane.

6. The method as claimed in claim 1, wherein the carbon content of the carbonaceous materials of the carbogenic nanoparticles is greater than or equal to 42% C and less than or equal to 50% C.

7. The method as claimed in claim 1, wherein the carbonaceous materials of the carbogenic nanoparticles have a nitrogen content that is greater than or equal to 3% N and less than or equal to 15% N.

8. The method as claimed in claim 1, wherein the diluent comprises one or more metal oxide-based and/or silicon oxide-based species.

9. The method as claimed in claim 1, wherein the diluent is or comprises a fingerprint powder.

10. The method as claimed in claim 1, wherein the carbonaceous materials of the carbogenic nanoparticles have a nitrogen content greater than or equal to 1% N and less than or equal to 11% N.

11. The method as claimed in claim 1, wherein the carbonaceous materials of the carbogenic nanoparticles further comprise nitrogen.

12. The method as claimed in claim 11, wherein the carbonaceous materials of the carbogenic nanoparticles have a nitrogen content greater than or equal to 1% N and less than or equal to 11% N.

13. The method of claim 1, wherein the method further comprises tape-lifting the imagable impression pattern of the latent fingerprint from the surface.

14. The method of claim 1, wherein the method further comprises imaging the imagable impression pattern of the latent fingerprint.

15. The method of claim 1, wherein the one or more carbogenic precursors are organic compounds comprising carbon, hydrogen, oxygen and nitrogen; and the carbonaceous material has, by elemental analysis, a carbon content between 40% C and 60% C, and a nitrogen content between 1% N and 20% N.

16. The method of claim 1, wherein carbonization of the one or more carbogenic precursors comprises pyrolysis of the one or more carbogenic precursors.

17. The method of claim 16, wherein pyrolysis of the one or more carbogenic precursors comprises heating the one or more carbogenic precursors at a temperature exceeding 180° C. but not exceeding 320° C.

18. The method of claim 16, wherein after pyrolysis, the resulting carbonized materials are purified, wherein purifying comprises one or more of:
1. forming a dispersion of the carbogenic nanoparticles in a solvent;
2. filtering the dispersion;
3. dialysing the dispersion;
4. refluxing in acid;
5. centrifuging to remove large particles.

19. The method of claim 1, wherein the one or more carbogenic precursors comprise at least a hydroxyl group; a carboxylic acid group or a salt or derivative thereof; and an amino group or a salt or derivative thereof.

20. The method of claim 1, wherein the one or more carbogenic precursors comprise citric acid or a salt or derivative thereof ethanolamine; or one or more products derived from a condensation reaction between citric acid and ethanolamine or a salt or derivative thereof.

21. The method of claim 1, wherein the one or more carbogenic precursors comprise biomass or one or more carbogenic precursors extracted from biomass.

22. The method of claim 1, wherein the one or more carbogenic precursors comprise one or more coupled carbogenic precursors, wherein the one or more coupled carbogenic precursors comprise non-carbogenic nanoparticles comprising carbogenic groups grafted to the surface thereof.

23. A fingerprint powder composition (FPC) for the visualization of latent fingerprints, which exhibits excitation-dependent emission and comprises;
at most 20 wt % carbogenic nanoparticles (CNPs) comprising carbonaceous material formed by carbonization of one or more carbogenic precursors, wherein the one or more carbogenic precursors are organic compounds comprising at least carbon, hydrogen, and oxygen; and
a diluent;
wherein the carbonaceous material has, by elemental analysis, a carbon content of less than or equal to 60% C.

24. The fingerprint powder composition of claim 23, wherein the carbonaceous materials of the carbogenic nanoparticles further comprise nitrogen.

25. The fingerprint powder composition as claimed in claim 24, wherein the carbonaceous materials of the carbogenic nanoparticles have a nitrogen content greater than or equal to 1% N and less than or equal to 11% N.

26. A method of preparing a fingerprint powder composition for the visualization of latent fingerprints, the method comprising providing carbogenic nanoparticles and blending the carbogenic nanoparticles with a diluent;
wherein the fingerprint powder composition exhibits excitation-dependent emission and comprises at most 20 wt % carbogenic nanoparticles comprising carbonaceous material formed by carbonization of one or more carbogenic precursors, wherein the one or more carbogenic precursors are organic compounds comprising carbon, hydrogen, and oxygen; and
wherein the carbogenic nanoparticles or carbonaceous material thereof has a carbon content of less than or equal to 60% C.

27. The method as claimed in claim 26, wherein carbonization of the one or more carbogenic precursors comprises pyrolysis of the one or more carbogenic precursors and/or carbogenic precursor groups.

28. The method as claimed in claim 27, wherein pyrolysis of the one or more carbogenic precursors and/or carbogenic precursor groups comprises heating the one or more carbogenic precursors and/or carbogenic precursor groups at a temperature exceeding 180° C. but not exceeding 320° C.

29. The method as claimed in claim 27, wherein after pyrolysis, the resulting carbonized materials are purified, wherein purifying comprises one or more of:
forming a dispersion of the carbogenic nanoparticles in a solvent in which the carbogenic nanoparticles are substantially insoluble;
filtering the dispersion;
dialysing the dispersion at a molecular weight cut off of at least 500 Daltons (Da) for a time sufficient to remove substantially all impurities and/or by-products having a molecular weight below the cut off;
fefluxing in acid;
fentrifuging to remove large particles.

30. The method as claimed in claim 26, wherein the carbogenic precursors and/or carbogenic groups comprise the elements carbon, hydrogen, oxygen, and nitrogen.

31. The method as claimed in claim 30, wherein the carbogenic precursors and/or carbogenic groups comprise at least a hydroxyl, a carboxy, and an amino group, and/or a suitable salt and/or derivative thereof.

32. The method as claimed in claim 31, wherein the carbogenic precursors and/or carbogenic groups comprise citric acid, ethanolamine, and/or one or more products derived from a condensation reaction between citric acid and ethanolamine, and/or a salt and/or derivative thereof.

33. The method as claimed in any of claims 30 to 32, wherein the carbogenic precursors and/or carbogenic groups comprise biomass and/or one or more carbogenic precursors and/or carbogenic groups extracted from biomass.

34. A fingerprint powder composition obtainable by the method of claim 26.

35. The method as claimed in claim 26, wherein the carbonaceous materials of the carbogenic nanoparticles further comprise nitrogen.

36. The method as claimed in claim 35, wherein the carbonaceous materials of the carbogenic nanoparticles habe a nitrogen content greater than or equal to 1% N and less than or equal to 11% N.

* * * * *